United States Patent
Phillips

(10) Patent No.: US 8,781,567 B2
(45) Date of Patent: *Jul. 15, 2014

(54) IMPLANTABLE MEDICAL DEVICES USING HEURISTIC FILTERING IN CARDIAC EVENT DETECTION

(71) Applicant: Cameron Health, Inc., San Clemente, CA (US)

(72) Inventor: James W. Phillips, Fountain Valley, CA (US)

(73) Assignee: Cameron Health, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/728,869

(22) Filed: Dec. 27, 2012

(65) Prior Publication Data

US 2013/0190634 A1 Jul. 25, 2013

Related U.S. Application Data

(63) Continuation of application No. 12/625,050, filed on Nov. 24, 2009, now Pat. No. 8,364,251, which is a continuation of application No. 11/497,204, filed on Aug. 1, 2006, now Pat. No. 7,623,913.

(51) Int. Cl.
A61B 5/0402 (2006.01)

(52) U.S. Cl.
USPC .......................................................... 600/517

(58) Field of Classification Search
USPC ....................................... 600/516–517; 607/9
See application file for complete search history.

(56) References Cited

U.S. PATENT DOCUMENTS 5,658,317 A * 8/1997 Haefner et al. ................... 607/5
5,662,688 A * 9/1997 Haefner et al. ................... 607/5

* cited by examiner

Primary Examiner — Luther Behringer
(74) Attorney, Agent, or Firm — Schwegman, Lundberg & Woessner, P.A.

(57) ABSTRACT

Methods for performing cardiac signal analysis in an implanted medical device, and devices configured to perform illustrative methods of cardiac signal analysis. A cardiac signal is captured by an implanted device using implanted electrodes and, during at least certain conditions, the cardiac signal undergoes heuristic filtering. In some embodiments, heuristic filtering is achieved by modifying a signal or value that is used as an indicator of received signal amplitude. In an illustrative example, the heuristic filtering includes periodically incrementing or decrementing the signal or value toward a desired quiescent point, where the heuristic filter period is significantly longer than the sampling period for the signal itself. In another illustrative example, the heuristic filter frequency can be adjusted dynamically to keep the signal average near the desired quiescent point.

19 Claims, 25 Drawing Sheets

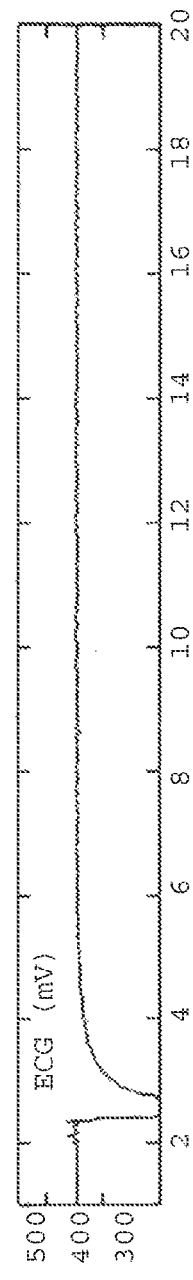
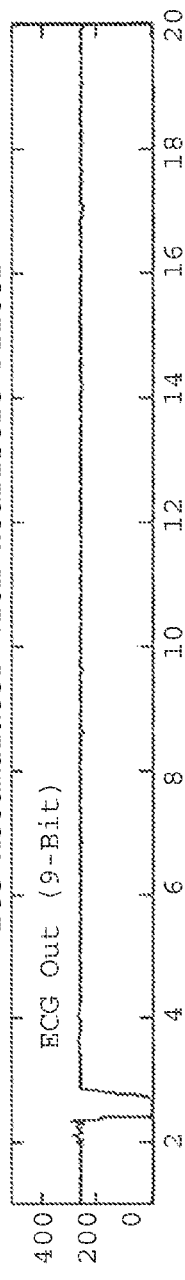
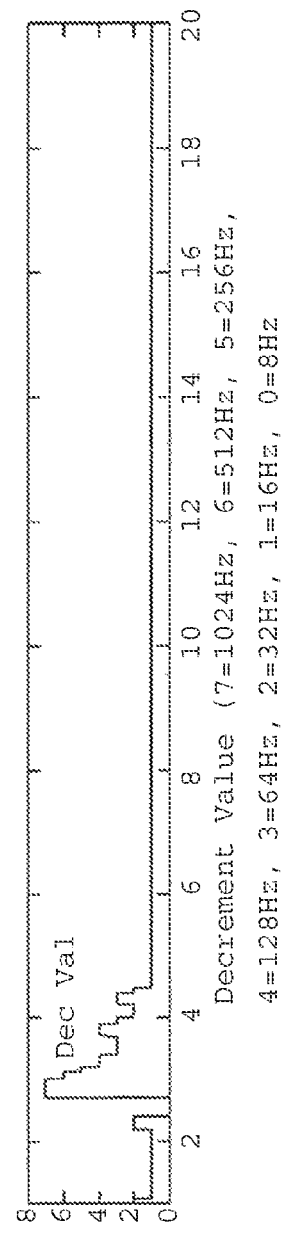
*Figure 10A*
*Figure 10B*
*Figure 10C*

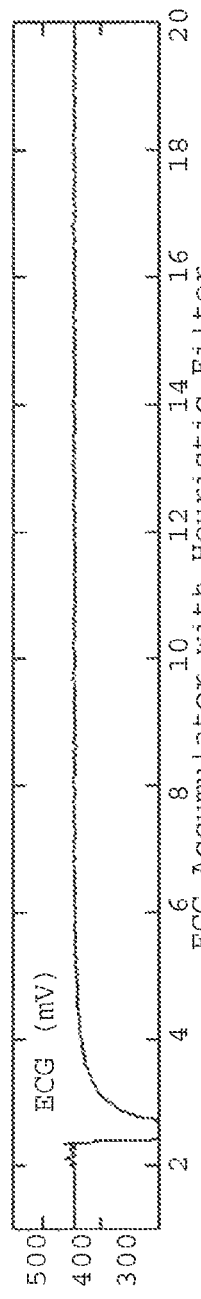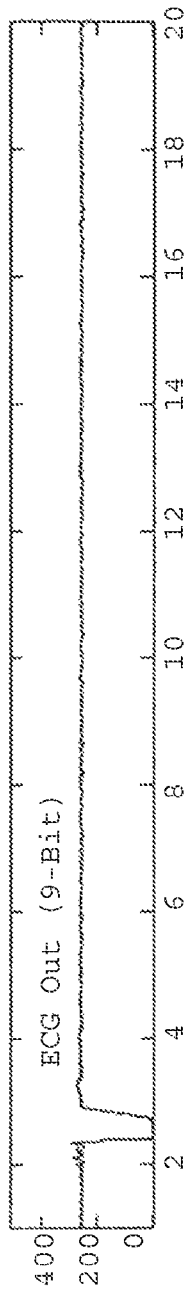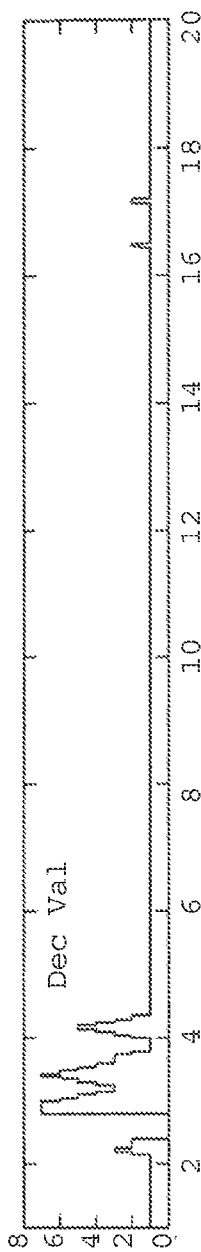
Figure 11A
Figure 11B
Figure 11C

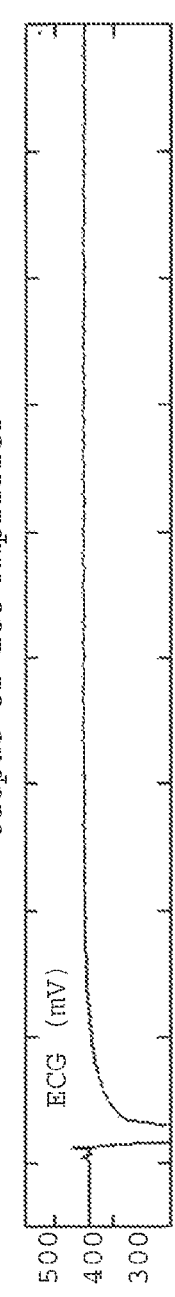
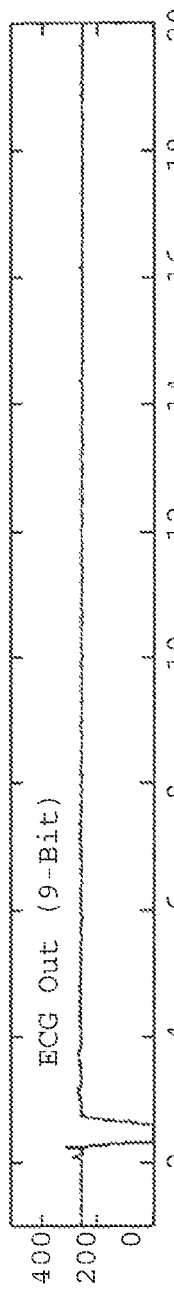
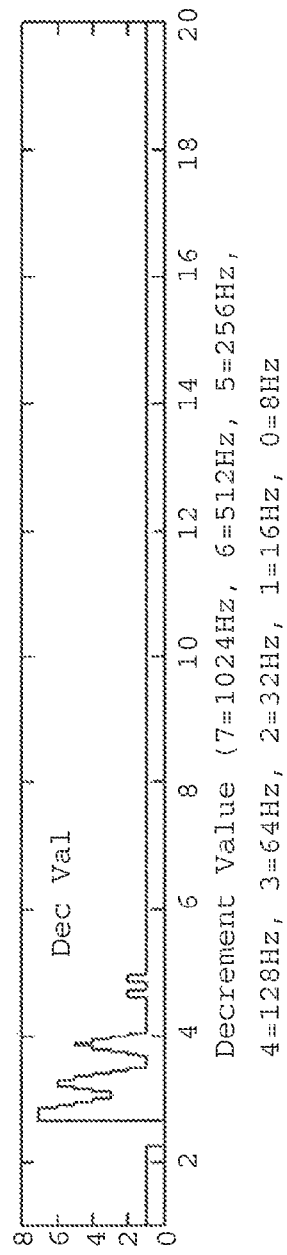
Figure 13A
Figure 13B
Figure 13C

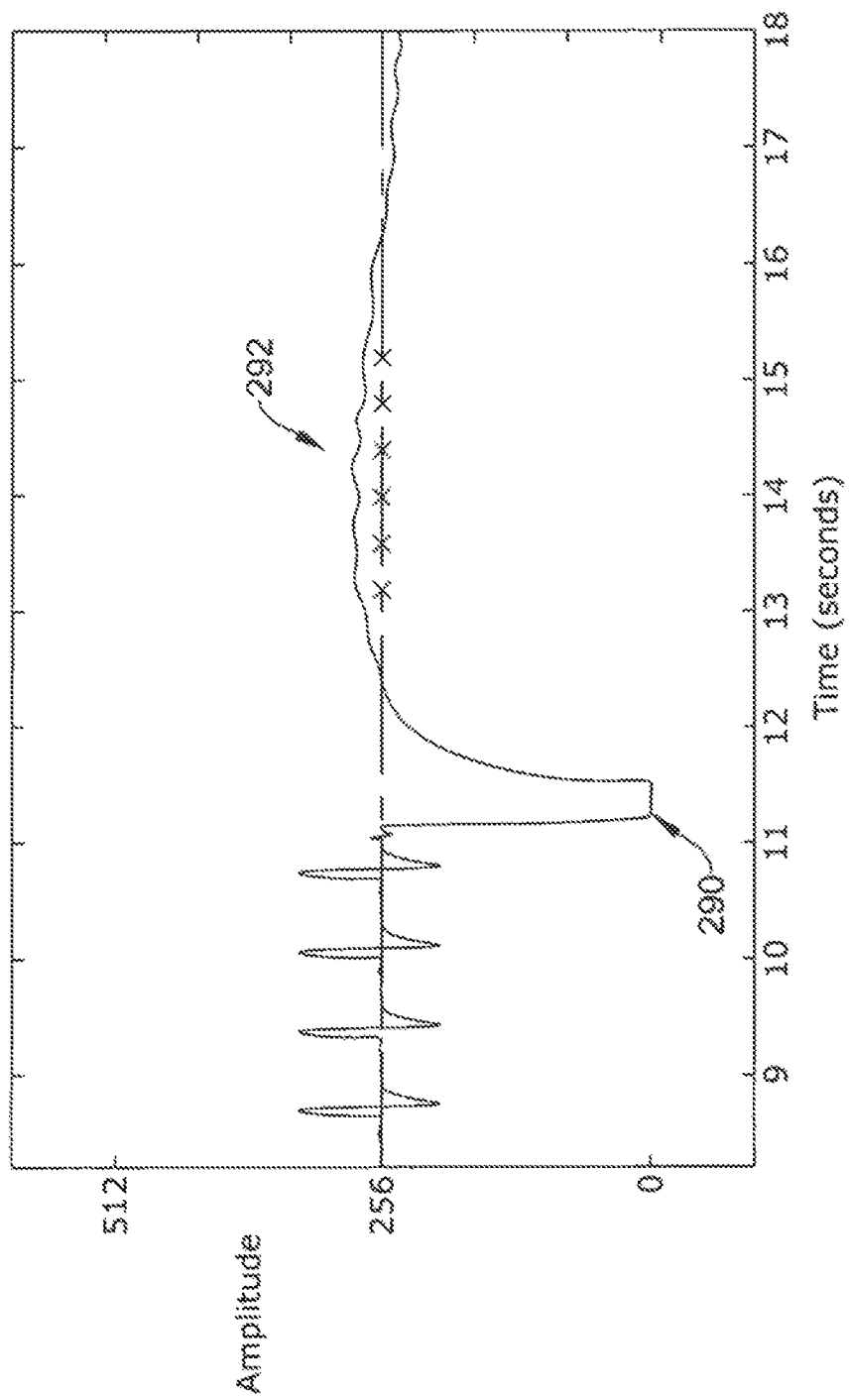

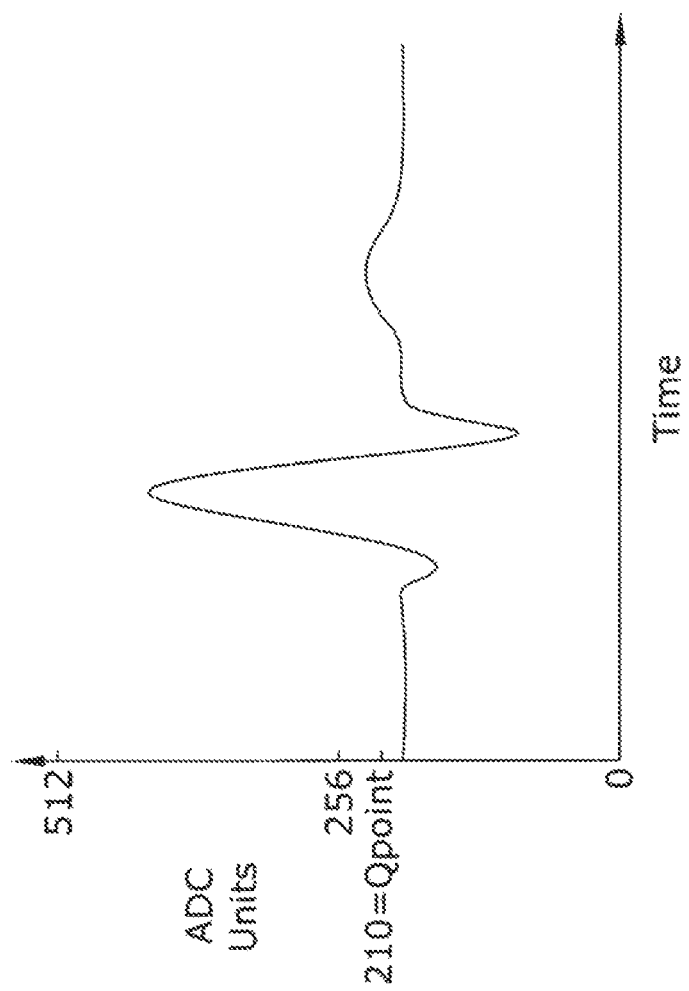

US 8,781,567 B2

IMPLANTABLE MEDICAL DEVICES USING HEURISTIC FILTERING IN CARDIAC EVENT DETECTION

RELATED APPLICATIONS

This application is a continuation of U.S. patent application Ser. No. 12/625,050, filed Nov. 24, 2009, published as US Patent Application Number 2010-0076515, now U.S. Pat. No. 8,364,251 and titled IMPLANTABLE MEDICAL DEVICES USING HEURISTIC FILTERING IN CARDIAC EVENT DETECTION, which is a continuation of U.S. patent application Ser. No. 11/497,204, filed Aug. 1, 2006, now U.S. Pat. No. 7,623,913 and also titled IMPLANTABLE MEDICAL DEVICES USING HEURISTIC FILTERING IN CARDIAC EVENT DETECTION, the disclosures of which are incorporated herein by reference.

FIELD

The present invention relates to the field of medical devices. More particularly, the present invention relates to the field of implantable medical devices including circuitry for capturing, detecting, and analyzing cardiac events using electrical signals.

BACKGROUND

Implantable medical devices that electronically monitor cardiac activity are desirable for a variety of purposes. Some such devices undergo, for various reasons, monitoring operations in which sensing and detection of cardiac events may be temporarily suspended or in which a sensing vector comes into use after a period of disuse. For example, an implantable cardioverter-defibrillator (ICD) may use a blanking period following delivery of an electrical stimulus. On return from the blanking period, reestablishment of a baseline for small-signal sensing of cardiac activity in a predictable and quick manner is desired.

SUMMARY

The present invention, in illustrative embodiments, includes methods for performing cardiac signal analysis in an implanted medical device, and devices configured to perform illustrative methods of cardiac signal analysis. A cardiac signal is captured by an implanted device using implanted electrodes and, during at least certain conditions, the cardiac signal undergoes heuristic filtering. In some embodiments, heuristic filtering is achieved by modifying a signal or value that is used as an indicator of received signal amplitude. In an illustrative example, the heuristic filtering includes periodically incrementing or decrementing the signal or value toward a desired quiescent point, where the heuristic filter period is significantly longer than the sampling period for the signal itself. In another illustrative example, the heuristic filter frequency can be adjusted dynamically to keep the signal average near the desired quiescent point.

BRIEF DESCRIPTION OF THE DRAWINGS

FIGS. 10A-10C, 11A-11C, 12A-12C, 13A-13C, 14A-14C and 15A-15C illustrate simulated analysis of cardiac signals following delivery of a shock, including analog ECG amplifier output, a digital representation of the cardiac signal, and the status of an associated heuristic filter;

FIGS. 16A-16B, 17A-17B and 18A-18B compare analysis with and without heuristic filters applied for select simulated cardiac waveforms;

FIG. 20 illustrates a method wherein the quiescent point is not centered on the ADC scale.

DETAILED DESCRIPTION

The following detailed description should be read with reference to the drawings. The drawings, which are not necessarily to scale, depict illustrative embodiments and are not intended to limit the scope of the invention.

As used herein, the term "heuristic" refers to a rule. A "heuristic filter" operates on the basis of a rule to adjust a value. This is in contrast to frequency selective filters that may be manifested in a number of ways in circuitry. For several of the examples given below, the heuristic of the heuristic filter is that a variable observed by the heuristic filter should be near a desired value. The meaning and application of this heuristic will become more apparent as the following description is read.

Figure 1A:
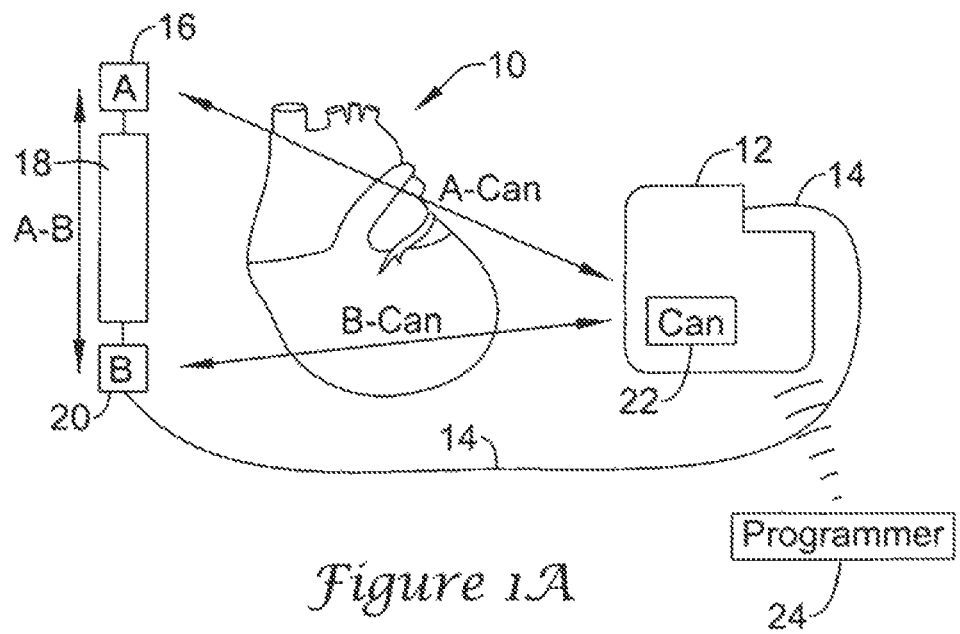
FIGS. 1A-1B illustrate, respectively, representative subcutaneous and intravenous ICD systems.
Figure 1B:
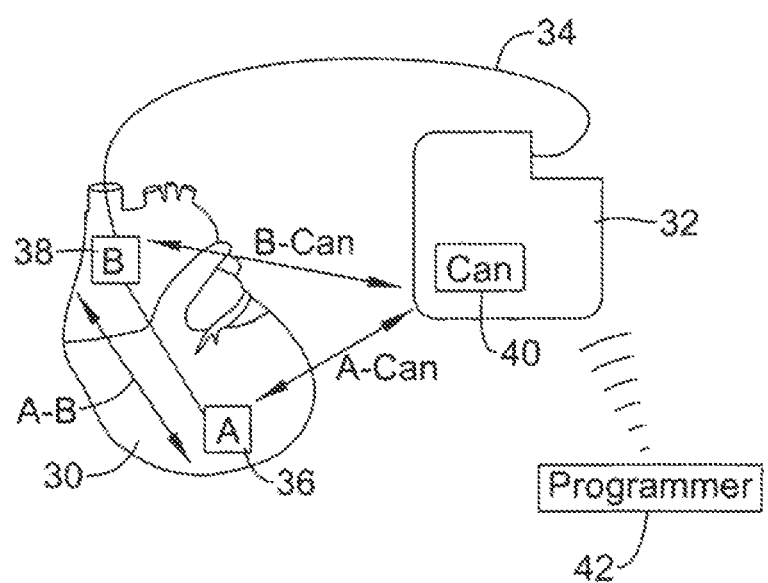

FIGS. 1A-1B, respectively, show subcutaneous and transvenous implanted cardiac stimulus systems relative to the heart. Referring to FIG. 1A, the patient's heart 10 is shown in relation to an implanted, subcutaneous cardiac stimulus system including a canister 12. A lead 14 is secured to the canister and includes sensing electrode A 16, coil electrode 18, and sensing electrode B 20. A can electrode 22 is shown on the canister 12.

Several vectors for sensing are therefore available including at least A-can, B-can, and A-B. It should be noted that the use of the coil electrode 18 as a sensing electrode is also possible. Illustrative subcutaneous systems are shown in U.S. Pat. Nos. 6,647,292 and 6,721,597, and the disclosures of these patents are incorporated herein by reference. Some embodiments include a unitary system having two or more electrodes on a housing as set forth in the '292 patent, rather than that which is shown. A unitary system including an additional lead may also be used.

Referring now to FIG. 1B, a transvenous system is shown relative to a patient's heart 30. The transvenous cardiac stimulus system includes a canister 32 connected to a lead 34. The lead 34 enters the patient's heart and includes electrodes A 36 and B 38. Additional electrodes for sensing or stimulus delivery may also be included in some embodiments of the present invention. In the illustrative example, electrode A 36 is located generally in the patient's ventricle, and electrode B 38 is located generally in the patient's atrium. The lead 34 may be anchored into the patient's myocardium. Again, a can electrode 40 is shown on the canister 32. With the transvenous system, plural sensing vectors may be defined as well.

For either subcutaneous or transvenous systems, a suitable method of selecting a sensing vector may be used, for example, as set forth in U.S. patent application Ser. No. 10/901,258, filed Jul. 27, 2004 and now U.S. Pat. No. 7,392, 085, which is incorporated herein by reference. In both FIGS. 1A and 1B, one or more sensing electrodes may also be used for stimulus delivery, and multiple possible stimulus delivery vectors may be defined.

The systems shown in FIGS. 1A-1B may include operational circuitry and a power source housed within the respective canisters. The power source may be, for example, a battery or bank of batteries. The operational circuitry may be configured to include such controllers, microcontrollers, logic devices, memory, and the like, as selected, needed, or desired for performing the illustrative methods set forth herein. The operational circuitry may (although not necessarily) further include a charging sub-circuit and a power storage sub-circuit (for example, a capacitor or a bank of capacitors) for building up a stored charge. The operational circuitry may also be adapted to provide a pacing output. Either or both cardioversion/defibrillation and pacing sub-circuitry and capacities may be incorporated into a single device. The methods discussed below may also be embodied in hardware within the operational circuitry and/or as instruction sets for operating the operational circuitry and/or in the form of machine-readable media (optical, electrical, magnetic, etc.) embodying such instructions and instruction sets.

Each of the devices 12, 32 may further include such components as would be appropriate for communication (typically via RF) with an external device such as a programmer. To this end, programmers 24 (FIG. 1A) and 42 (FIG. 1B) are also shown. For example, during an implantation procedure, once the implantable device 24, 42 and leads (if included) are placed, the programmer 24, 42 may be used to activate and/or direct and/or observe diagnostic or operational tests. After implantation, the programmer 24, 42 may be used to noninvasively determine the status and history of the implanted device 12, 32 and to upgrade programming of the implanted device 12, 32. The programmer 24, 42 and the implanted devices 12, 32 are adapted for wireless communication allowing interrogation of the implanted device(s). The programmers 24, 42 in combination with the implanted devices 12, 32 may also allow annunciation of statistics, errors, history and existing or potential problems to the user/physician.

Figure 2:
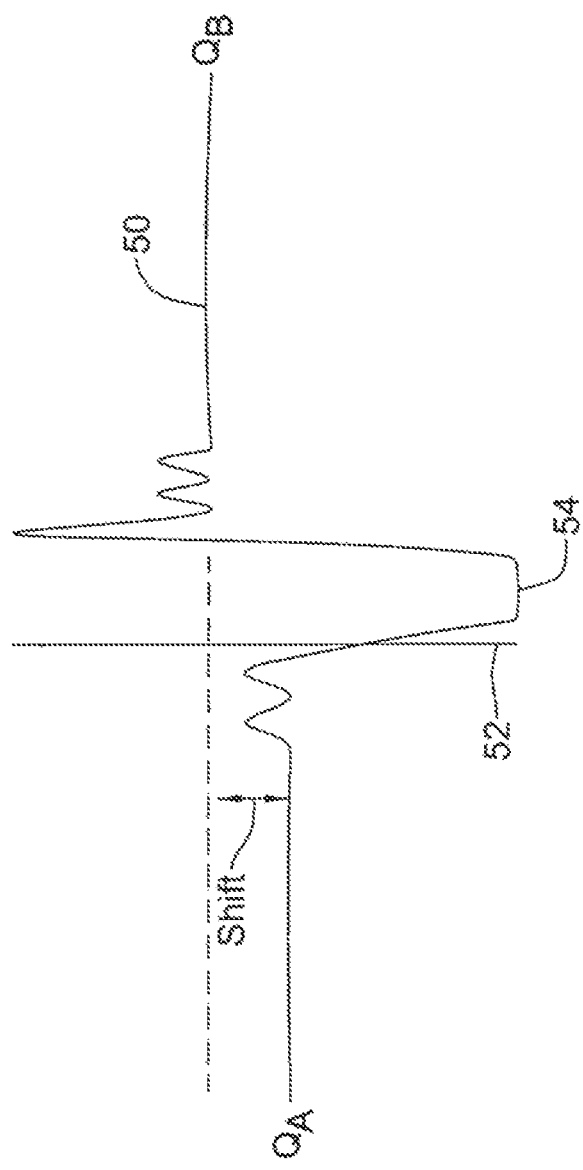
FIG. 2 illustrates the effect of post-shock afterpotential on cardiac monitoring in an implantable medical device system.

FIG. 2 illustrates the effect of post-shock afterpotential on cardiac monitoring in an implantable medical device system. A rough cardiac signal, which could be sensed by implanted electrodes, is shown generally at 50, with a shock being delivered at time 52, resulting in saturation 54. Prior to shock delivery, the signal 50 traverses a path, in accordance with the patient's cardiac functions, about a first quiescent point QA, while after the shock delivery, the signal 50 oscillates about a second quiescent point QB. The result is a shift in the baseline.

Figure 3:
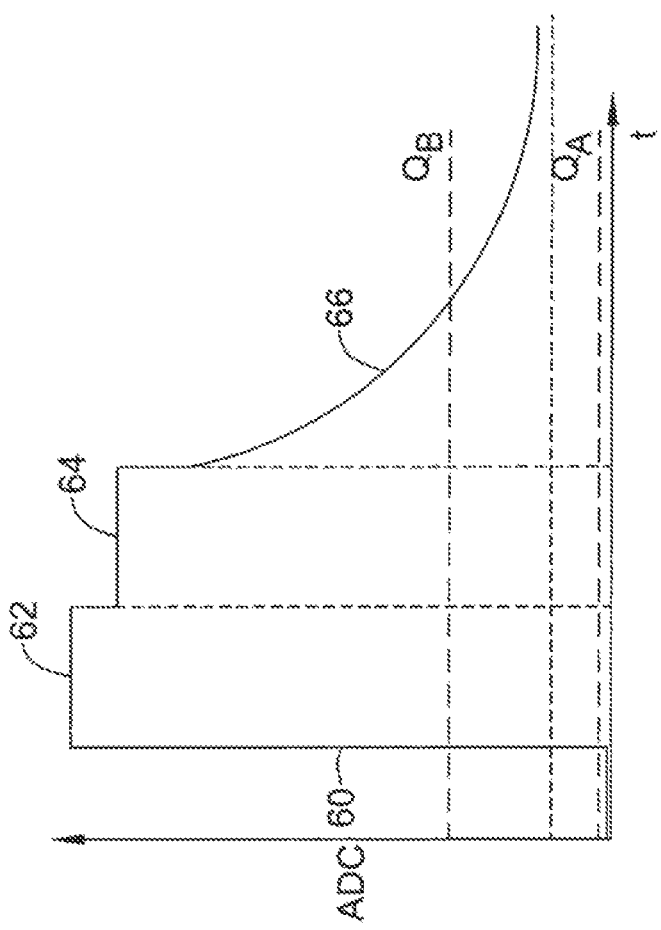
FIG. 3 is a graph of an illustrative detection profile.

The baseline shift may become relevant when cardiac event detection is occurring. Referring to FIG. 3, a detection profile is shown generally by line 60. The detection profile is used to determine whether and when the received cardiac signal likely indicates a cardiac event. When the detection profile 60 is crossed by the incoming signal, a detection occurs. The existence of a detection starts analysis of the signal near the detection. The detection profile 60 includes a refractory period 62 during which detections do not occur. The refractory period 62 follows a previous detection. The illustrative detection profile 60 includes a continuation period 64 that follows the refractory period 62, during which the detection threshold remains relatively high. The detection profile includes a decay period 66, during which the detection threshold follows an exponentially decaying profile toward a detection floor. The particulars of a detection profile 60 may be selected as desired.

As can be seen, the detection profile 60 is configured to work well when a first quiescent point QA exists. However, the second quiescent point QB can cause a detection profile 60 to be crossed even without a cardiac event occurring. It may be desirable for the system to operate with a consistent quiescent point that readily aligns with the detection profile 60.

Figure 4A:
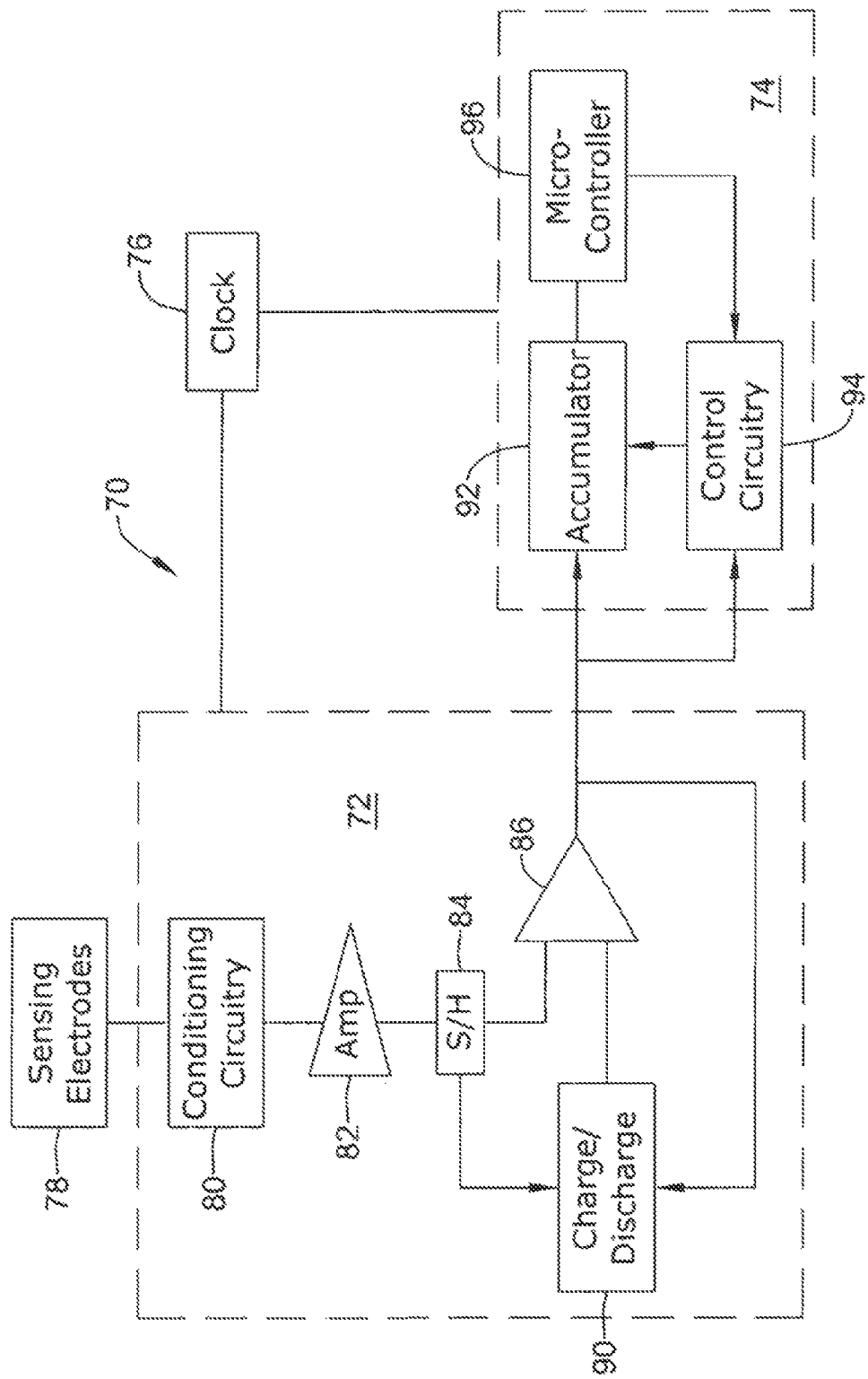
FIG. 4A illustrates a first signal analysis system.

Some embodiments of the present invention are adapted for use with an analog-to-digital converter (ADC) similar to that illustrated in commonly assigned U.S. Pat. No. 6,927, 721, titled LOW POWER A/D CONVERTER, the disclosure of which is incorporated herein by reference. FIG. 4A illustrates an example of a non-conventional ADC as part of analysis system 70. The illustrative analysis system 70 includes an analog chip 72 and digital chip 74. A clock 76 is also shown and may be provided on either chip or, as shown, may be separately provided. The clock 76 may allow synchronization of certain processes on each chip 72, 74.

Sensing electrodes 78 capture an electrical signal from implanted positions in a patient. The electrical signal is received by conditioning circuitry 80 (such as DC-blocking capacitors and other filtering devices, pull-up or pull-down resistors, switching circuitry allowing for selection and/or blanking of appropriate sensing vectors, and other suitable circuitry) and supplied to an amplifier 82. The amplifier 82 provides an output to sample and hold (S/H) circuitry 84. The S/H circuitry 84 provides an output to one input of a comparator 86. The other input for the comparator 86 is coupled to charge/discharge circuitry 90.

The charge/discharge circuitry 90 may include, for example, a comparator providing an output to a capacitor via a resistor such that the input to the comparator 86 is the voltage that is stored on the capacitor. In another embodiment, the charge/discharge circuitry includes a digital-to-analog converter (DAC) and an associated up/down counter such that the output of the DAC is controlled by the output of the counter, wherein the counter counts up or down depending on whether the output of the comparator 86 is high or low after each new sample occurs. Once the output of the comparator 86 switches, the charge/discharge circuitry 90 latches to hold its output stable until a next sample is indicated by the S/H circuitry 84.

When a new sample is received by the S/H 84, a latch in the charge/discharge circuitry 90 is set/reset, and the output of the comparator 86 is used to determine whether the new sample has a greater or lesser voltage than the previous voltage. If the new sample has a higher voltage, the output of the comparator 86 goes high, causing the charge/discharge circuitry 90 to increase the voltage it supplies to the comparator 86 until it equals the new sample. At this time, the output of the comparator 86 switches, indicating to the charge/discharge circuitry 90 that charging/discharging is to stop. If the new sample has a lower voltage, the output of the comparator 86 goes low, causing the charge/discharge circuitry 90 to perform the reverse steps. Again, the output of the comparator switches, indicating to the charge/discharge circuitry 90 that charging/discharging is to stop.

The digital chip 74 includes an accumulator 92, control circuitry 94, and a microcontroller 96. The control circuitry 94 may be synchronized with the S/H 84 in an appropriate manner. For example, both may receive a signal from the microcontroller 96 indicating a new sample is to be taken. The control circuitry 94, when a new sample is supplied by S/H 84 to comparator 86, determines whether the output of the comparator 86 is high or low. If the comparator 86 output is high, the control circuitry 94 causes the accumulator 92 to increment its stored value until the comparator 86 output switches. If the comparator 86 output is low, the control circuitry 94 causes the accumulator 92 to decrement its stored value until the comparator 86 output switches.

One or both of the speed of the charge/discharge circuitry 90 and/or the speed at which the comparator 86 counts up or down can be slew-rate limiting for this ADC. Rather than direct measurement of the received signal, this ADC provides an output determined by the relative change in the input from one sample to the next. Thus there may be uncertainty in the output when saturation occurs and/or when the input voltage changes in excess of the slew rate. In particular, referring back to FIG. 2, the ADC may not return to the original quiescent point QA following saturation 54. A heuristic filter that adjusts the ADC accumulator toward a single quiescent point removes this variability.

Figure 4B:
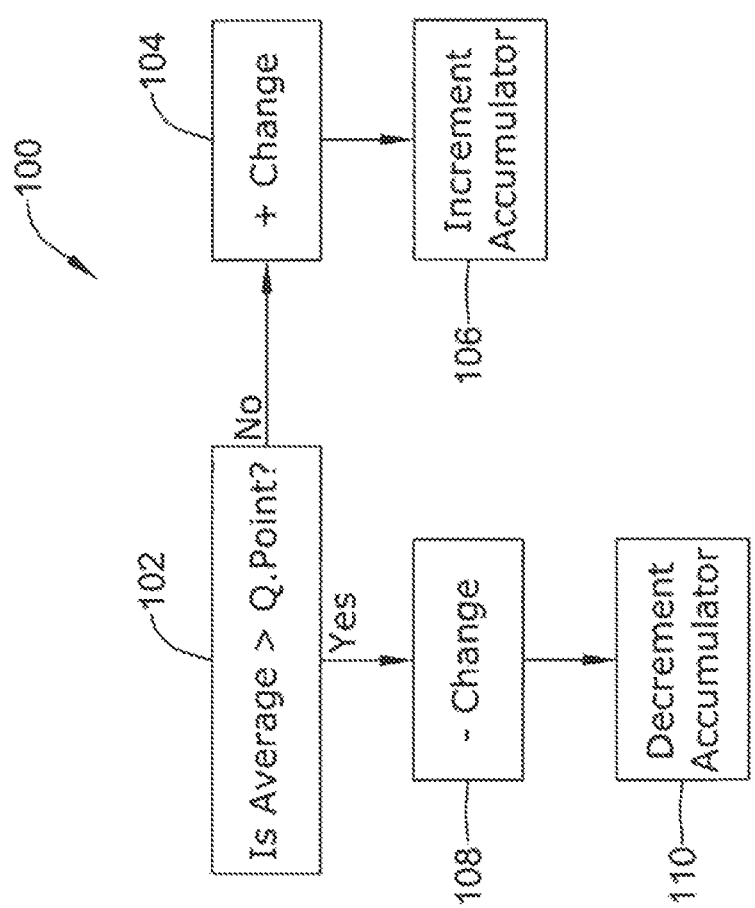
FIG. 4B is a block diagram illustrating a method of heuristic filtering for the signal analysis system of FIG. 4A.

FIG. 4B illustrates a method of operating a heuristic filter in association with the ADC shown in FIG. 4A. The method 100 first compares a value to the variable Q.Point, as shown at 102. This comparison at 100 may be a simple comparison of a most recent sample to the Q.Point. Alternatively, and as shown in FIG. 4B, some methods use a different value, "Average," which may be the average of a previous number of digital signal samples. Any appropriate number of samples may be selected. In an illustrative example, 25 previous samples may be averaged in a system taking samples at 256 Hz, spanning a period of about 100 milliseconds, which may be long enough to span any cardiac or noise event. An "average" of only the most recent signal would also include an embodiment in which only a single sample is considered.

In the illustrative embodiment, Q.Point is a desired quiescent point for the accumulator or ADC. Q.Point may be at or near the center of the dynamic range of the accumulator. In an illustrative example, a 9-bit accumulator is used and 256, the center of the accumulator range, is selected as the Q.Point. Other accumulator sizes may be used. Also, an off-center quiescent point may also be chosen, as shown below in FIG. 20.

If the Average is equal to or below the Q.Point, a positive change is indicated, as shown at 104, and the accumulator is incremented as shown at 106. Otherwise, a negative change is indicated, as shown at 108, and the accumulator is decremented, as shown at 110.

In an illustrative example, the heuristic filter can be either enabled or disabled, and it is called periodically. For example, the heuristic filter may operate at 16 Hz, giving a periodicity of 62.5 milliseconds. In this manner, when the heuristic filter is enabled, each time it is called, it moves the accumulator either up or down depending on whether the previous Average of the accumulator is less than or greater than the quiescent point. If operating at 16 Hz, the heuristic filter would be called 16 times per second. If the ADC is operating away from the desired quiescent point, the heuristic filter will repeatedly move the accumulator toward the quiescent point. If the ADC is away from the quiescent point due to normal R-wave fluctuations, the heuristic filter may cause the ADC output to overshoot somewhat when the ADC returns to the quiescent point.

A later example will illustrate a dynamic heuristic filter in which the frequency or periodicity of the heuristic filter is changed as well.

Figure 5A:
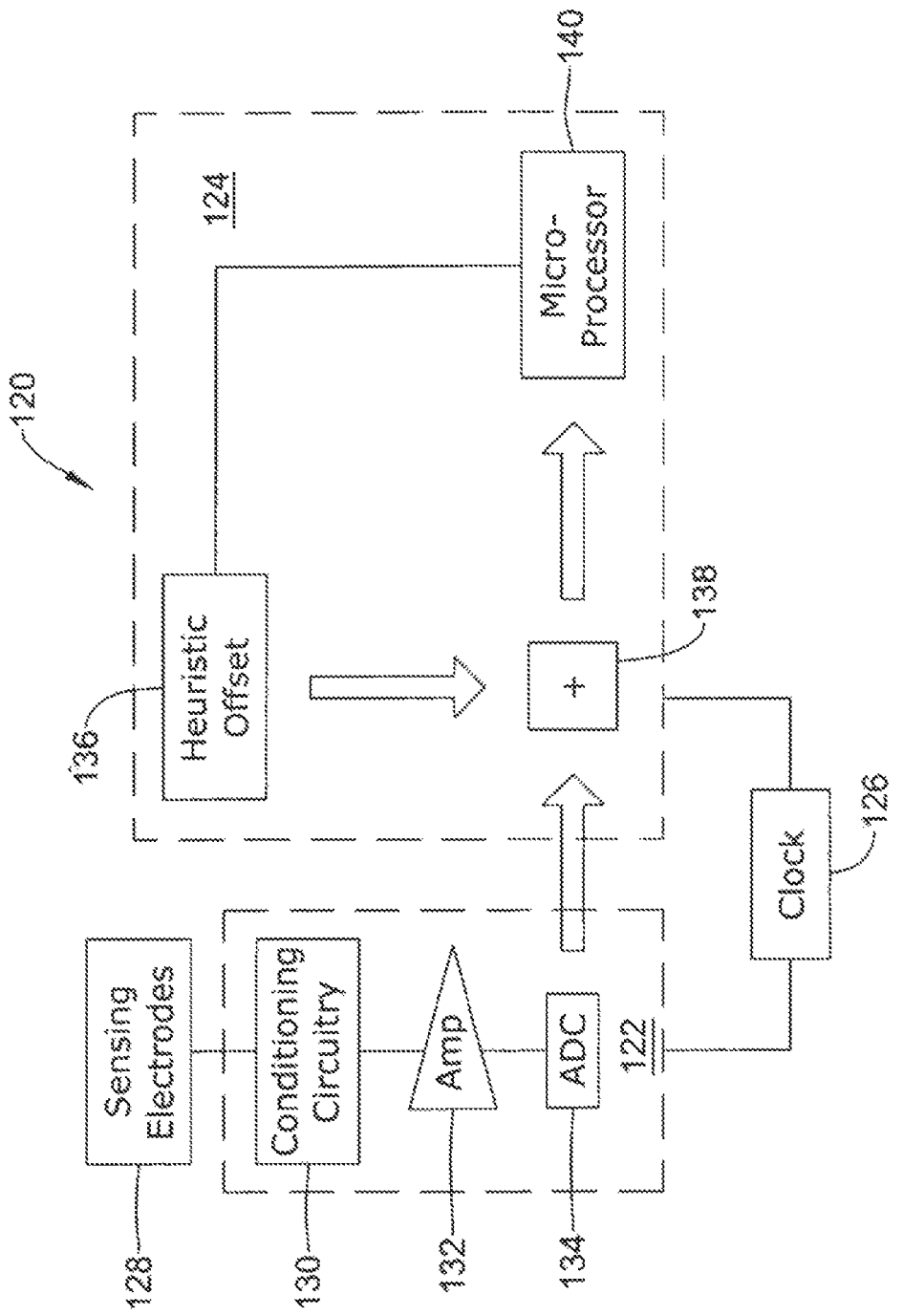
FIG. 5A illustrates a second signal analysis system.

FIG. 5A illustrates a second signal analysis system. The system 120 includes an analog chip 122 and a digital chip 124, as well as a clock 126 that may be on either chip 122, 124 or may be separately provided. A signal is captured from implanted sensing electrodes 128 using conditioning circuitry 130, which may be similar to that shown in FIG. 4A. The signal then goes to an amplifier 132, which feeds an output to ADC 134 (an S/H sub-circuit may also be included, or the ADC may be a latched or gated ADC). The ADC 134 may be a successive approximation ADC or any other suitable ADC. The ADC 134 provides a signal to the digital chip 124.

The digital chip 124 includes heuristic offset circuitry 136, an adder 138, and a microprocessor 140. The heuristic offset circuitry 136 may be a register/accumulator that stores a value (the heuristic offset) used to offset the output of the ADC toward a desired quiescent point. Thus, the adder 138 adds the output of the ADC and the heuristic offset circuitry 136, and provides the result to the microprocessor 140.

Figure 5B:
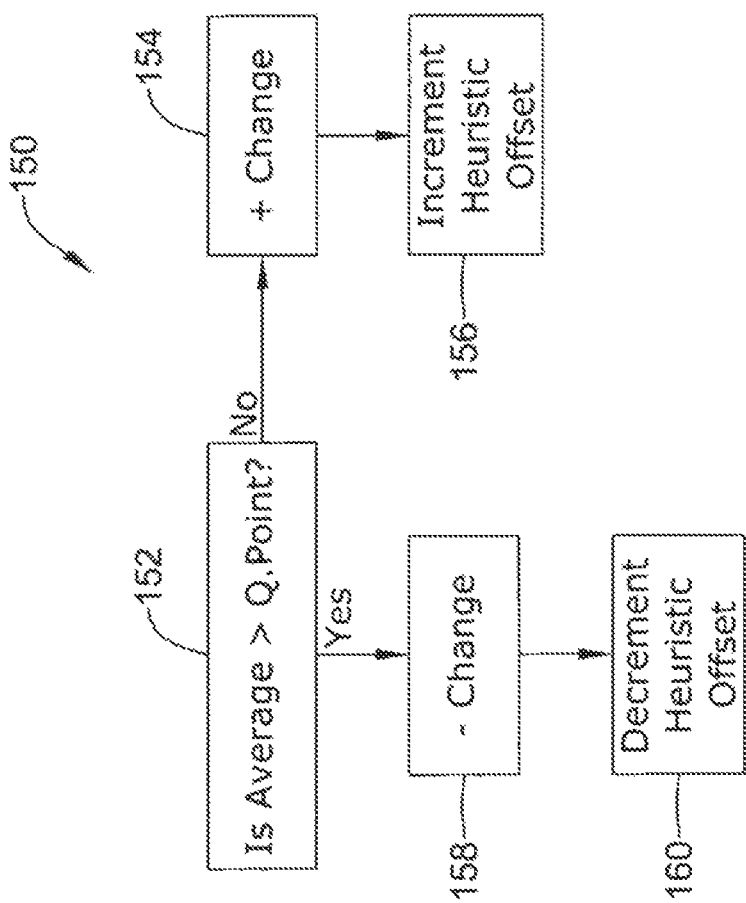
FIG. 5B is a block diagram illustrating a method of heuristic filtering using a heuristic offset for the signal analysis system of FIG. 5A.

FIG. 5B is a block diagram illustrating a method of heuristic filtering using a heuristic offset for the system of FIG. 5A. The method 150 first determines whether a value "Average" is greater than a variable "Q.point". Again, if desired, the "Average" may cover any suitable number of samples, or may be replaced by a single value from a most recent sample. The Q.Point, as before, is a desired quiescent point. If the Average is equal to or less than the Q.Point, a positive change is indicated, as shown at 154, and the heuristic offset is incremented, as shown at 156. This pushes the sum from adder 138 (FIG. 5A) up in value. If, instead, the Average is above the Q.Point at 152, a negative change is indicated, as shown at 158, and the heuristic offset is decremented, as shown at 160. Because the output of the ADC in FIG. 5A is direct, rather than indirect as in FIG. 4A, an offset is used, rather than an adjustment to the ADC itself. The offset may also be used in association with the device of FIG. 4A.

Figure 6:
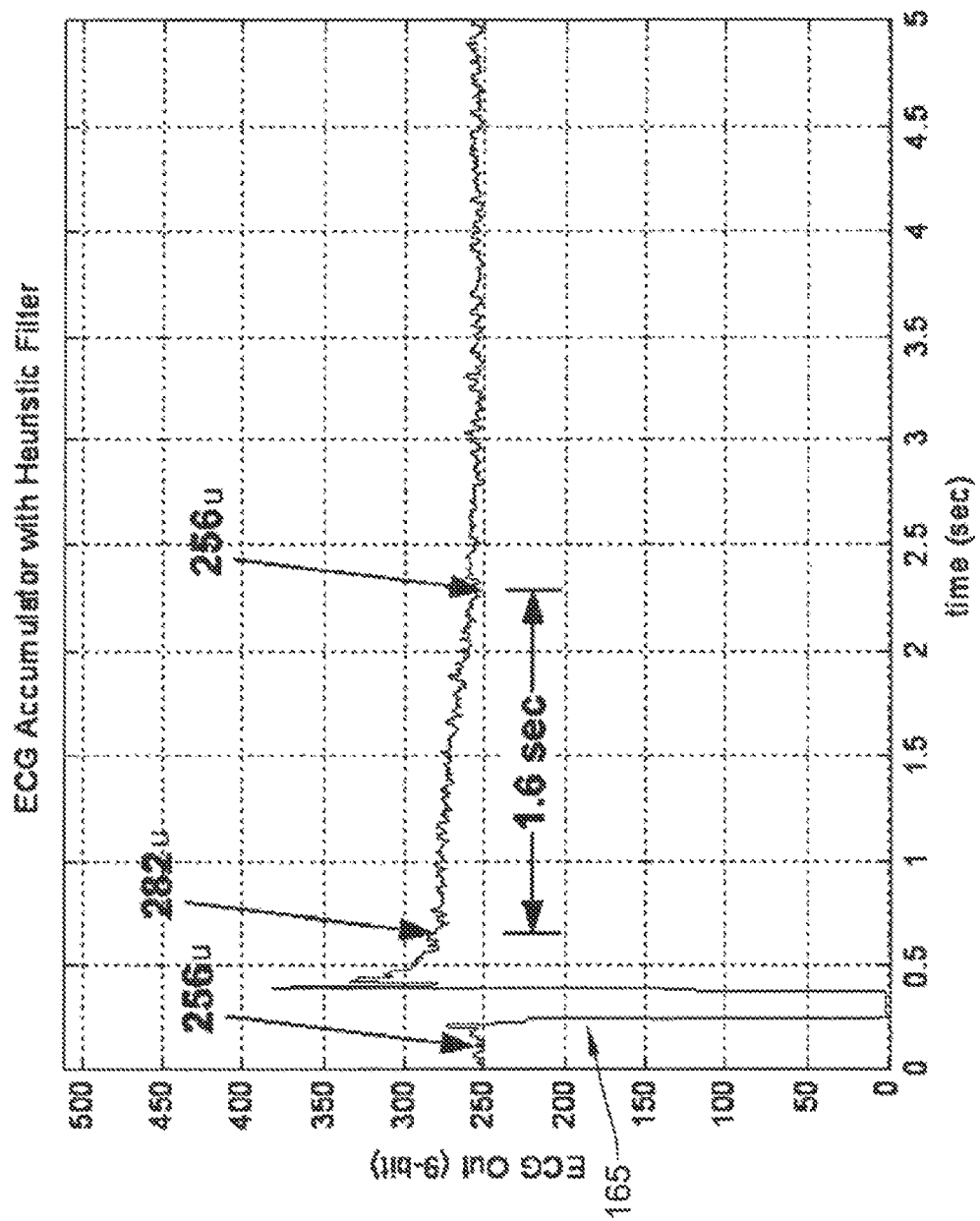
FIG. 6 is a graphical example of an ECG accumulator output with heuristic filtering applied.

The method 100 may be executed by the control circuitry 94 or the microcontroller 96 (FIG. 4A), which may direct the accumulator 92 to increment or decrement, for example. In another example, the system of FIG. 4A may instead use a heuristic offset (FIGS. 5A-5B), which can be maintained and calculated internal to the microcontroller 96. In yet another example, the accumulator 92 may itself be incorporated into the microcontroller 96, which may perform the method 100 internally or may instead perform a method using a heuristic offset (FIGS. 5A-5B). FIG. 6 illustrates ECG analysis using heuristic filtering. The illustrative example follows the model of FIG. 4A, with an accumulator holding an ADC output value on the digital chip. A 9-bit accumulator is assumed, with a dynamic range as shown of 0-512 units. A shock is delivered at 165, causing saturation of the system inputs.

Prior to shock delivery 165, the average, over time, of the accumulator output was 256 units, as indicated. However, after shock delivery 165, the system recovers to an average of about 282 units. The heuristic filter, operating at 16 Hz, returns the system to an average of 256 units. In the illustrative example, the system takes about 1.6 seconds to recover from 282 units to 256 units.

Figure 7:
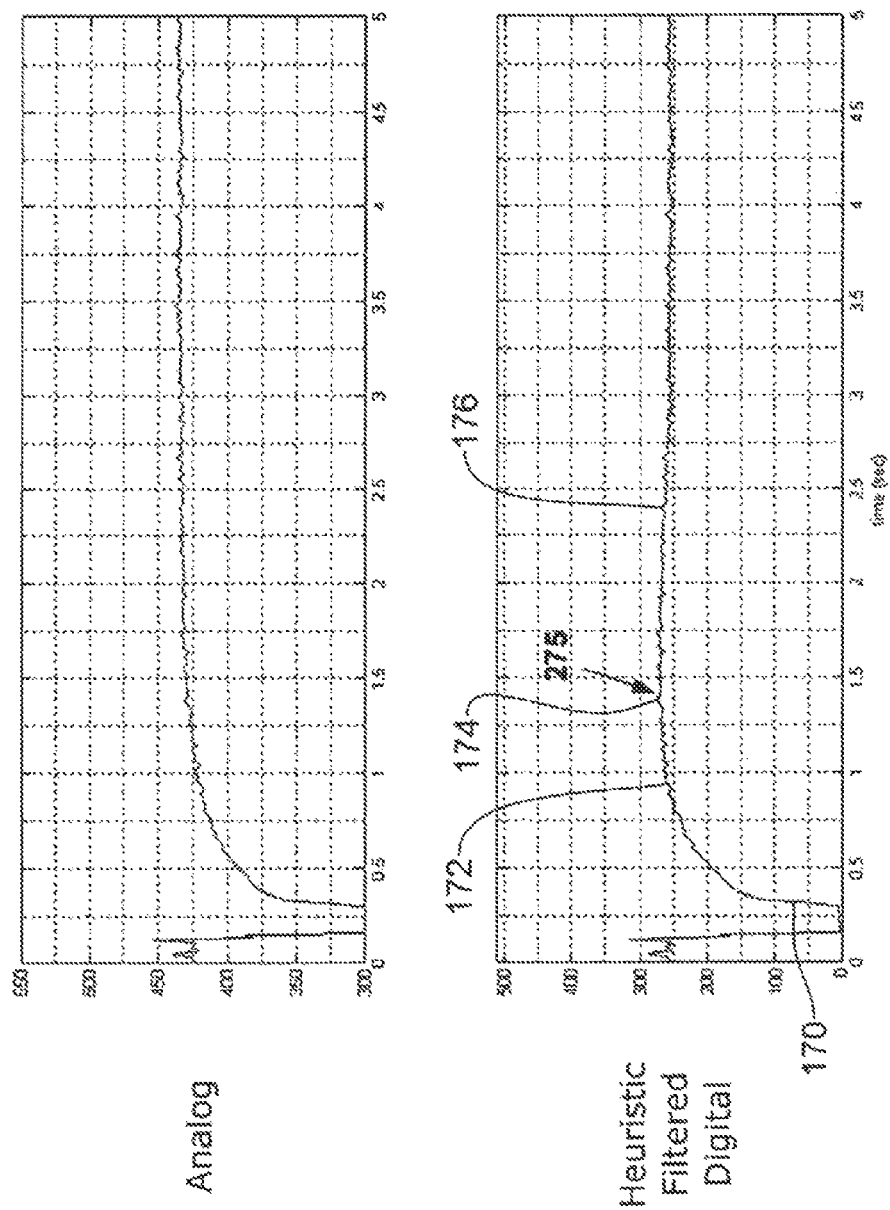
FIG. 7 compares an analog ECG signal to a corresponding digital signal after heuristic filtering.

FIG. 7 compares an analog ECG signal to a corresponding ECG circuit output after heuristic filtering. In the illustrative example of FIG. 7, the system undergoes a shock at about t=0.1 seconds. As indicated in the analog signal graph, there is a slow recovery for the analog signal to a relatively flat period starting at about 1.5 seconds.

The lower graph indicates a Heuristic-filtered digital signal. After the shock, the digital signal initially recovers more quickly, as shown at 170. By the time indicated at 172, the heuristic filter and/or the ADC operation have returned to the center point of the 9-bit output. However, the analog signal has not recovered to its fully relaxed state, and the continuing rise of the analog signal pushes the digital signal above the quiescent point. Further, at time 172, if an "Average" of previous values is used to make the heuristic filter determination of whether to increment or decrement the ADC accumulator (or increase or decrease the heuristic offset), the heuristic filter will also contribute to overshoot as shown at 174. After the overshoot peaks at 274 units, as indicated, the system then recovers, as shown at 176, to relatively steady state.

To prevent the overshoot shown in FIG. 7, some illustrative examples further include a dynamic heuristic filter in which the frequency of the heuristic filter changes as the quiescent point is approached.

Figure 8:
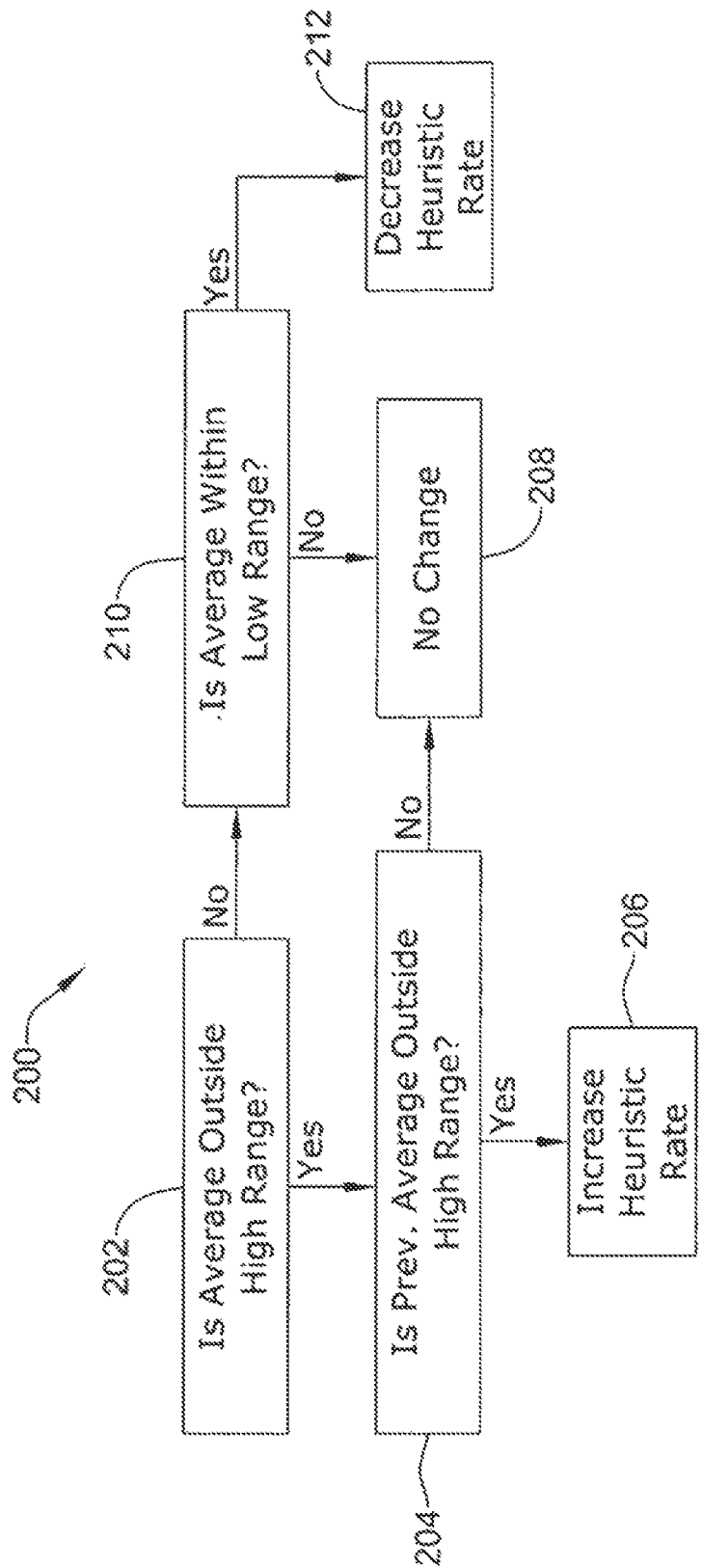
FIG. 8 is a block diagram for an illustrative method of dynamic heuristic filtering.

FIG. 8 is a block diagram showing operation of an illustrative heuristic filter. The method 200 begins by comparing the Average of N previous sample amplitudes (or magnitudes, if desired) to a predetermined High Range variable, as shown at 202. The number N of samples used in the Average for this stage may be selected to span a typical R-wave, for example, at 256 Hz, 25 samples would represent 100 ms of signal, wide enough to span most R-waves. The High Range variable determines whether the Average is far enough away from the desired quiescent point that an increase toward the maximum heuristic filter rate is desirable. If the Average is outside the High Range at 202, the method continues to 204 and determines whether the Previous Average was also outside the High Range. If so, then the heuristic rate is increased, as shown at 206. Two checks are taken before an increase in the heuristic rate in this illustrative example; if desired, a single check may be performed. The double check makes the heuristic filtering more conservative, while still allowing recovery when the Average fails to return toward the quiescent point.

In an illustrative example, the heuristic rate is scaled from 0 to 7 as follows:

| Heuristic Filtering Level | Actual Rate (Hz) |
|---|---|
| 0 | 8 |
| 1 | 16 |
| 2 | 32 |
| 3 | 64 |
| 4 | 128 |
| 5 | 256 |
| 6 | 512 |
| 7 | 1024 |

Different scales may be used, as desired. If, for example, the heuristic filtering is operating at level 4, then the heuristic filter is called at a rate of 128 Hz, or every 7.8 ms. Supposing a 9-bit accumulator and a desired quiescent point of 256 digital units, a High Range could be 240-272. Then, if the Average=232, and previous Average=231, the heuristic filtering would be changed to level 5 at step 206, increasing the rate to 256 Hz. This example uses a relatively wide High Range. Another illustrative example uses a narrower High Range, such that for a 9-bit accumulator having a desired quiescent point of 256 digital units, the illustrative example has a High Range of 252-260 digital units. If a larger accumulator were used (such as a 12-bit accumulator), the range of available frequencies may be increased.

If the double check at 204 fails, then no change occurs, as shown at 208. If the Average is not outside the High Range at 202, then it is determined whether the Average is within the Low Range, as shown at 210. If so, then the Heuristic Rate is decreased, as shown at 212. Again supposing a 9-bit accumulator and a desired quiescent point of 256 digital units, a Low Range could be 254-258 digital units. If the heuristic filtering is operating at level 4 and the Average=255 digital units, the method would reach step 212 and decrease the heuristic filtering to level 3. A wider or narrower Low Range may also be used. If the Average is not within the Low Range at 210, then no change occurs, as shown at 208.

Figure 9:
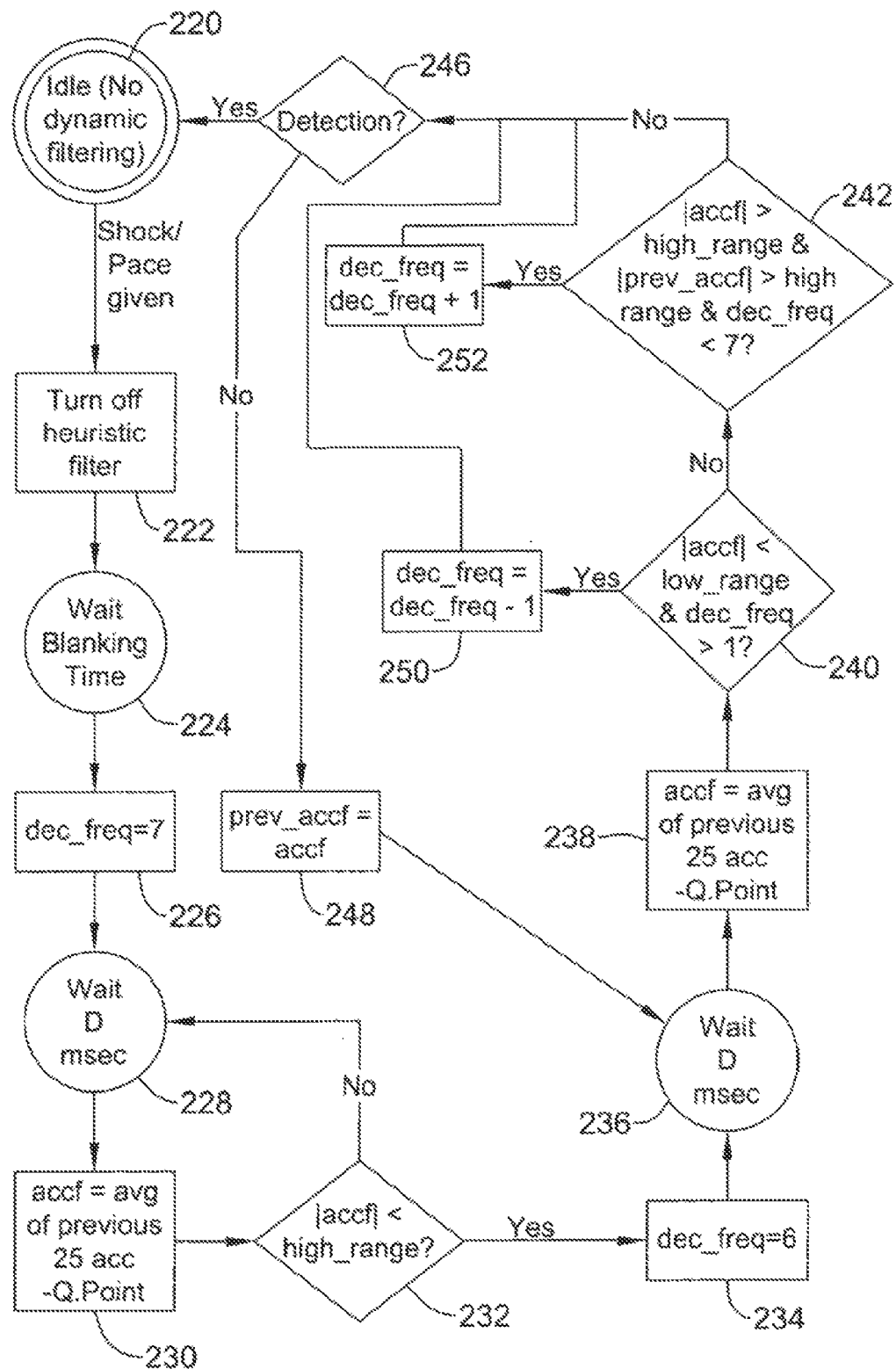
FIG. 9 is a block diagram for an illustrative method of dynamic heuristic filtering.

FIG. 9 is a block diagram for a method of dynamic heuristic filtering. The method illustrated in FIG. 9 provides a detailed illustration that applies the method of FIG. 8 to a system such as that shown in FIGS. 4A-4B. The method in FIG. 9 includes an Idle block, as illustrated at 220, during which there is no dynamic heuristic filtering occur. After a shock or pace is given, the method goes to step 222, wherein the heuristic filter is turned off as the shock is given and during a blanking period that follows the shock, as indicated at 224. Next, a variable dec_freq is set to 7, as shown at 226. Dec-freq is a variable indicating the state or frequency of the heuristic filter. In the illustrative embodiment, the above table of heuristic filter frequencies is used, with setting 7 being the highest frequency of operation. In the example, step 226 sets the dynamic heuristic filter to its highest frequency following the blanking time after a shock is delivered.

The method then enters a loop comprising steps 228, 230, 232. The wait state 228 occurs for a predetermined time period. The illustrative analyses shown below in FIGS. 10-19 A-C alternate between D=50 ms and D=100 ms and show that the selection of one or the other may affect the output. As shown at 230, a variable accf is set to the average of the previous 25 accumulator values (the previous sampled signal amplitudes), less the desired quiescent point. Thus, accf provides the difference between the average of the sampled signal and the desired quiescent point. Next, the absolute value of accf is compared to a variable, high_range, as shown at 232. In an illustrative example, a 9-bit accumulator is used, with a centered quiescent point at 256 digital units, and high_range is set to 4. Different sizes and ranges may be used, and the quiescent point need not be centered on the digital scale, although it often will be.

The loop of steps 228, 230, 232 continues until accf falls within high_range and the condition at 232 is met. The method then reduces the frequency of the heuristic filter by setting dec_freq=6, as shown at 234. The method then enters another loop including steps 236, 238, 240, 242, 246, 248, 250, and 252.

The second loop begins with a wait state 236 which, as with step 228 occurs for a predetermined period of time such as 50 ms or 100 ms, although other values may also be used. Next, accf is calculated, as before, as shown at 238. Then, as shown at 240, the absolute value of accf is compared to a variable, low_range, and it is determined whether dec_freq is greater than one. The variable low_range is set to 2 in an illustrative embodiment. In the illustrative example, the lowest value that dec_freq can have is 1, thus the second condition on step 240. If either condition fails at 240, the method continues to step 242.

At step 242, the absolute value of accf is compared to high_range, the absolute value of the previous accf is compared to high_range, and it is determined whether dec_freq is less than 7. As before in FIG. 8, both the present and previous values of accf must fall outside of the high range to trigger an increase in dec_freq. Also, the maximum value for dec_freq in this illustrative example is 7. The double-check of accf and previous accf may be omitted, and a single check of accf may be performed instead. The specific range/values for dec_freq may also vary in additional embodiments. Again, if either condition fails at 242, the method continues to step 246.

In step 246, it is determined whether a detection has occurred. If a detection has occurred, the dynamic heuristic filter is disabled and the method returns to the idle state at 220. Otherwise, the method continues to step 248 where the previous accf value is updated to the most recently calculated accf. The method then returns to the wait state at 236 and waits for the next iteration. In another embodiment, a detection may trigger an interrupt that places the heuristic filter in the idle state 220.

Going back into the loop, if the conditions at 240 are both met, it is determined that the frequency of the heuristic filter may be lowered to avoid overshooting the quiescent point and limiting any resulting oscillation. Thus, as shown at 250, dec_freq is reduced by one. The method then goes to step 246 as before. If, instead, the conditions at 242 are met, it is determined that the detection architecture/hardware has moved away from the quiescent point sufficiently to justify increasing the frequency of the heuristic filter. Therefore, dec_freq is increased by one, and the method goes to step 246 as before. In this manner, the heuristic frequency is dynamically changed until a detection occurs.

In the example of FIG. 9, the variables high_range and low_range are considered thresholds for comparison to accf, which is a variable that is related to the amplitude of the detected cardiac signal that is received from implanted electrodes.

Figure 12A:
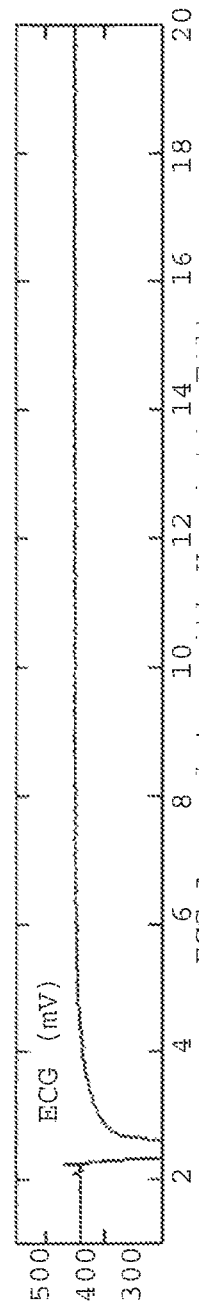
Figure 12B:
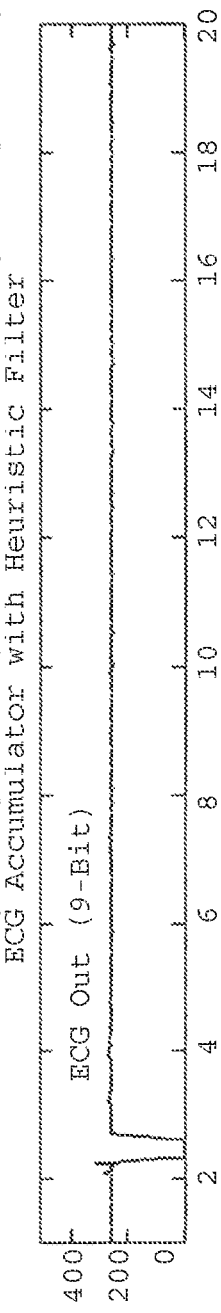
Figure 12C:
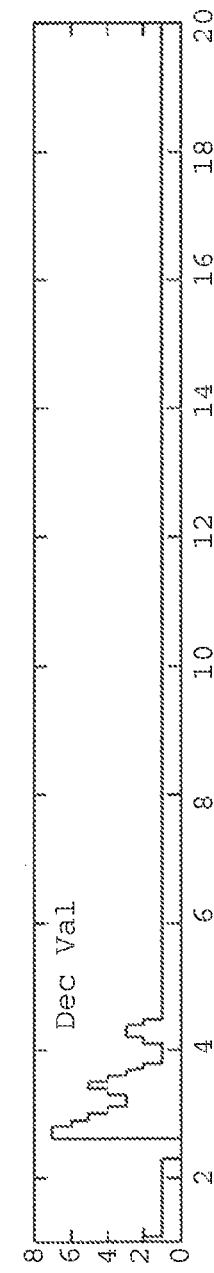
Figures 14A, 14B, 14C:
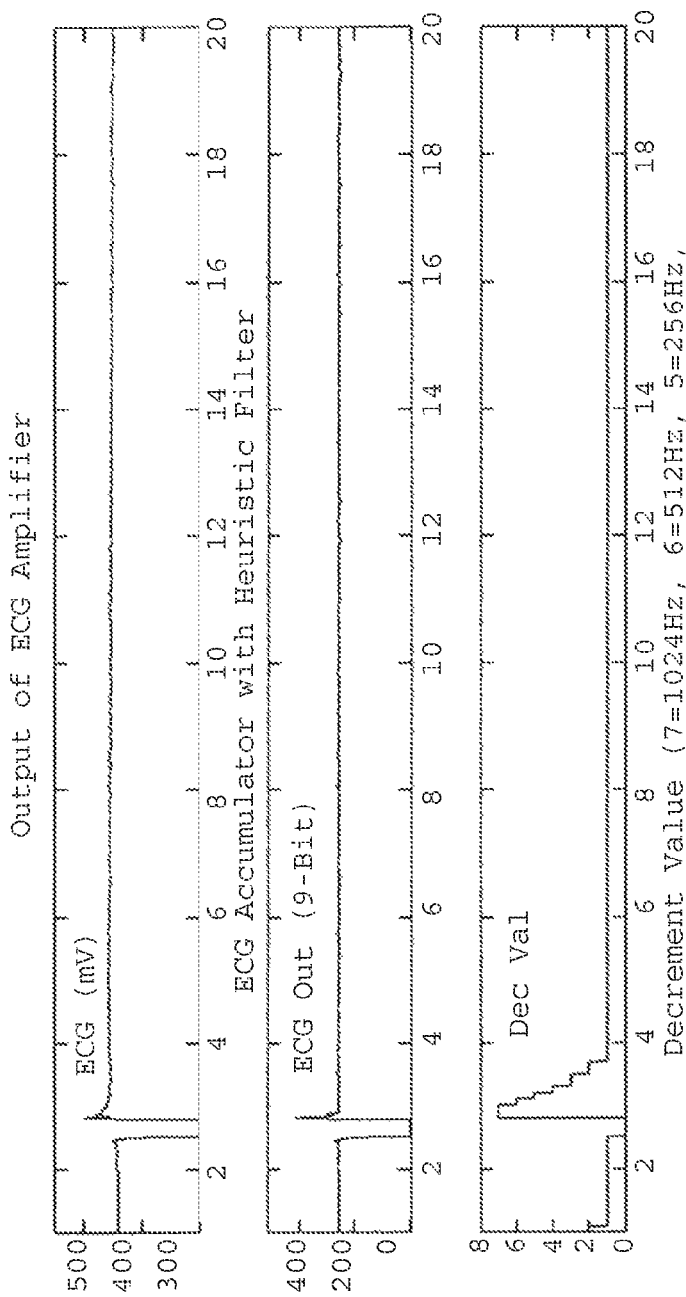

FIGS. 10A-10C, 11A-11C, 12A-12C, 13A-13C, 14A-14C and 15A-15C illustrate simulated analysis of cardiac signals following delivery of a shock, including analog ECG amplifier output, a digital representation of the cardiac signal, and the status of an associated heuristic filter. Each is based on a device using the ADC as shown in FIG. 4A. FIGS. 10A-10C, 12A-12C and 14A-14C each use D=100 ms, while FIGS. 11A-11C, 13A-13C and 15A-15C each use D=50 ms. The signal analyzed in FIGS. 10A-10C is the same as for 11A-11C, while the signal analyzed in FIGS. 12A-12C is the same as for 13A-13C, and the signal analyzed in FIGS. 14A-14C is the same as for 15A-15C.

FIG. 10A illustrates the output of the ECG amplifier, while FIG. 10B shows the output of the ECG accumulator, and FIG. 100 illustrates the state of the heuristic filter. It can be seen that the recovery, post shock, of the output of the ECG amplifier slopes up to a steady value (FIG. 10A), while the ECG accumulator provides a sharper output (FIG. 10B) and returns to a quiescent point much more quickly. The state of the heuristic filter includes some ringing as shown in FIG. 100. While FIGS. 10A-10C use D=100 ms, using D=50 ms as shown in FIGS. 11A-11C causes the heuristic filter to reach dec_freq=1 more quickly, although a higher amplitude ringing occurs between approximately t=4.0 s and t=4.25 s.

FIGS. 12A-12C show another example waveform and analysis with D=100 ms, while FIGS. 13A-13C show the same waveform with analysis at D=50 ms. More ringing can be observed than in the examples of FIGS. 10A-10C and 11A-11C. In each of the examples of FIGS. 10A-10C, 11A-11C, 12A-12C and 13A-13C, the ECG amplifier output gradually returns from a lower amplitude up to a settling point. It appears that the D=100 ms analysis performs more effectively for this waveform, as there is less ringing and the accumulator output is relatively flat.

Figure 15A:
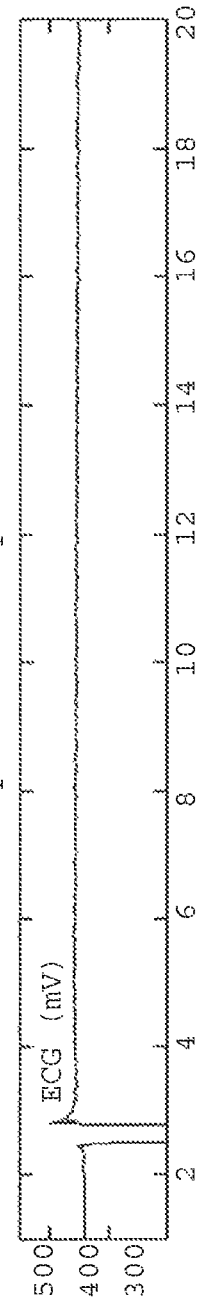
Figure 15B:
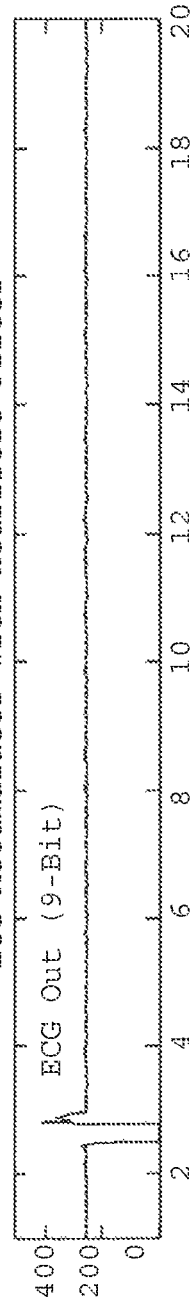
Figure 15C:
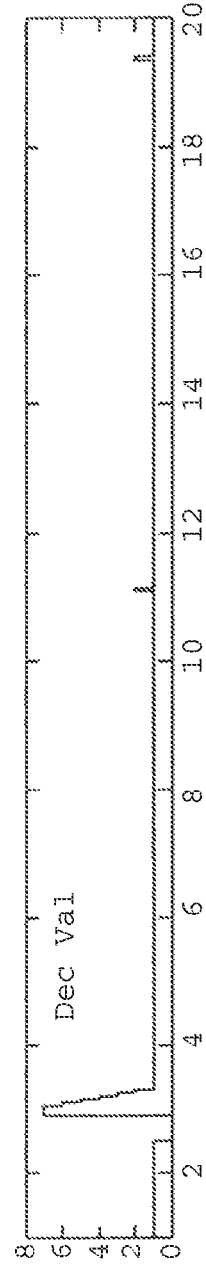

In contrast, the waveform of FIGS. 14A and 15A quickly returns to a higher amplitude than before the shock delivery and remains relatively flat after some initial ringing. For this waveform, as shown by FIGS. 14B-14C and 15B-15C, the lower D=50 ms analysis provides arguably better results by returning the filter to dec_freq=1 more quickly, although the accumulator signal does not settle as quickly as for the D=100 ms analysis.

While the simulations of FIGS. 10A-10C, 11A-11C, 12A-12C, 13A-13C, 14A-14C and 15A-15C appear to indicate that D=100 ms provides better performance, this may depend upon the waveform at issue as well as the particulars of the system under consideration, including amplifier and electrode gain/loss, sampling frequency, and other variables.

Figure 16A:
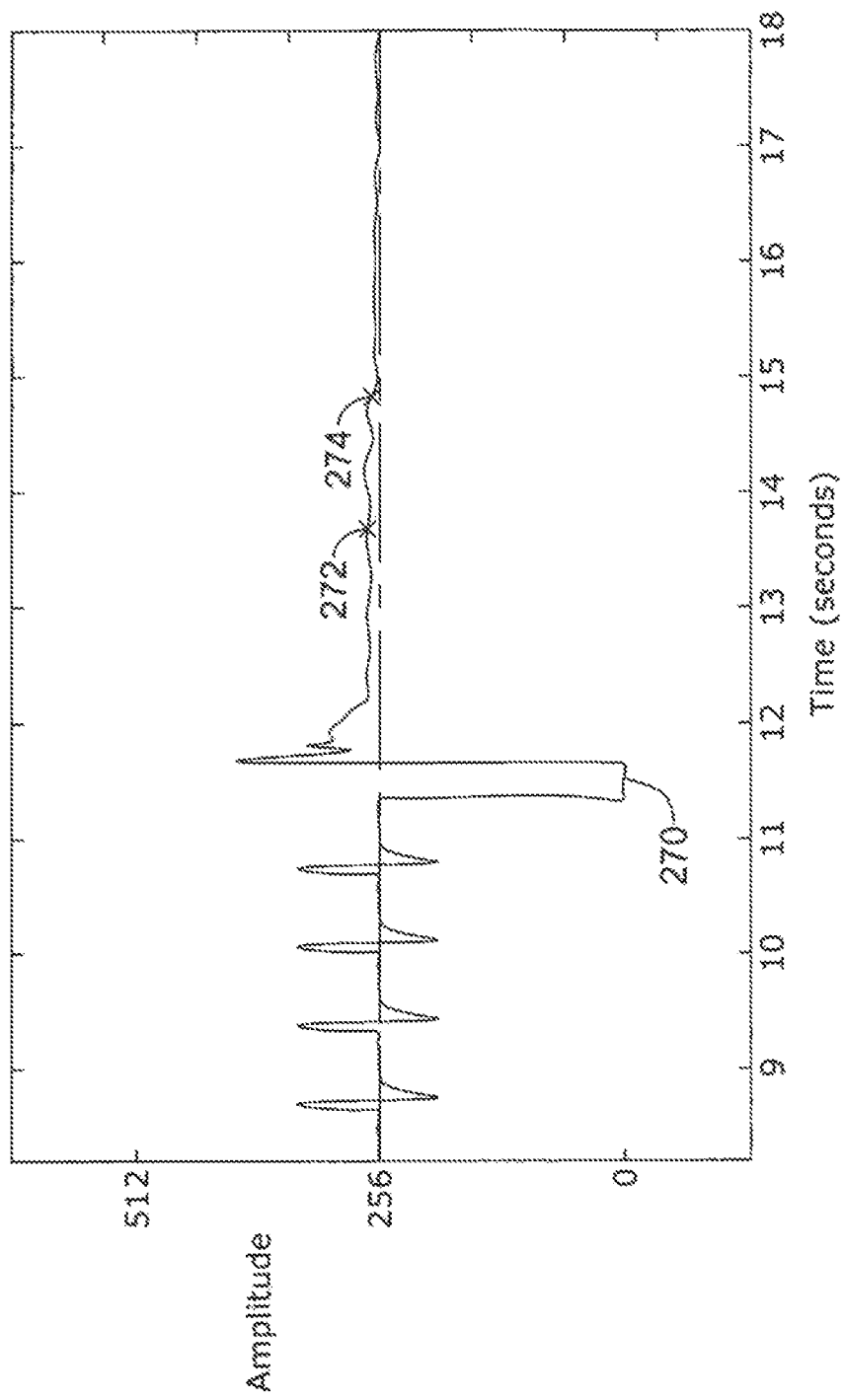

FIGS. 16A-16B, 17A-17B and 18A-18B compare analysis with and without heuristic filters applied for select simulated shocking waveforms. Referring to FIG. 16A, a simulated waveform was created by overlaying a normal sinus QRS signal onto a portion of a blank signal with a shock and recovery portion therein. The initial QRS allows for establishment of sensing parameters using a detection profile as shown above in FIG. 3. The QRS is applied for the four beats shown on the left, and terminates at about t=11 seconds. Thus, any detection occurring after the shock is applied at 270 is a false detection.

Figure 16B:
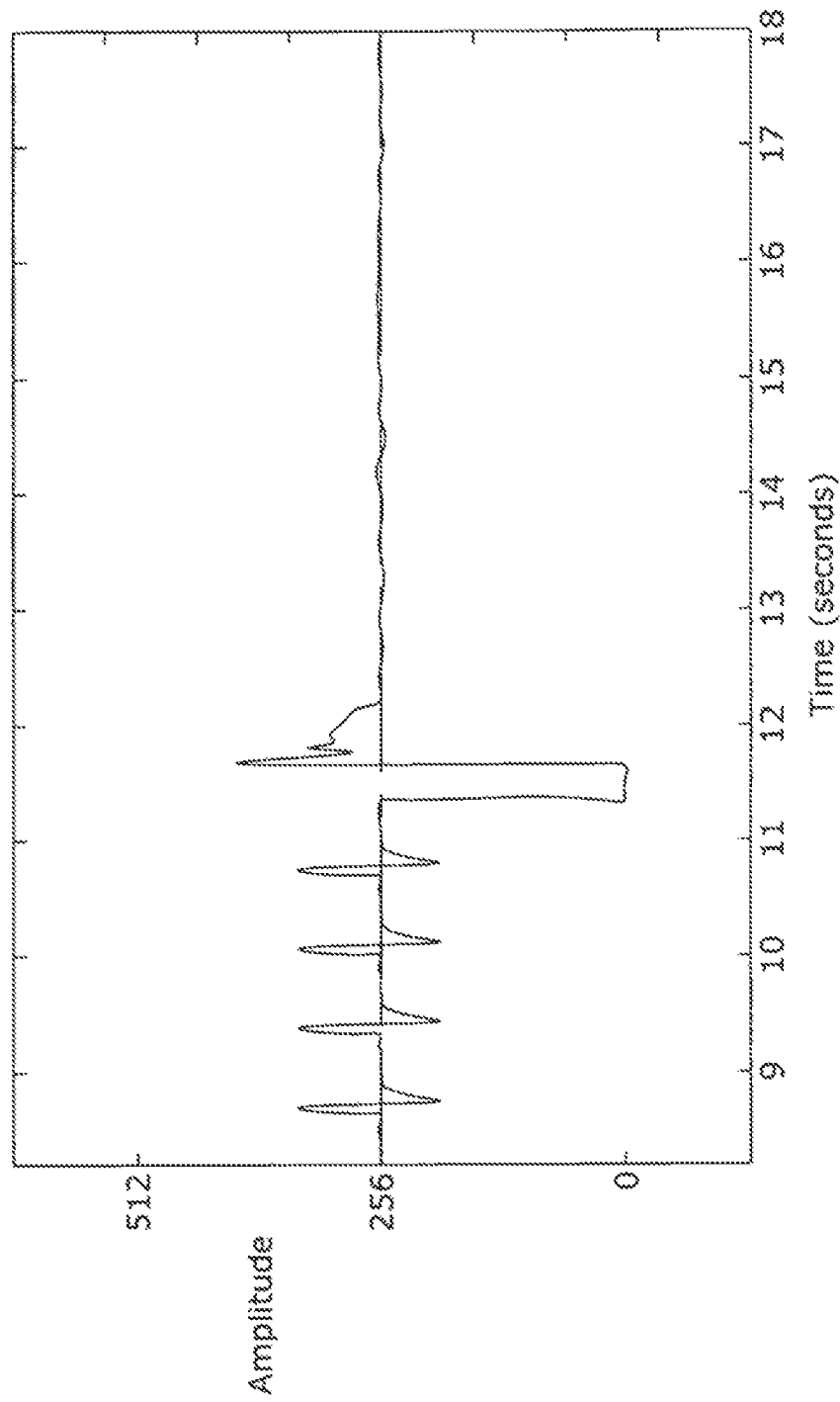

FIG. 16A illustrates analysis with the heuristic filter turned off. As can be seen, false detections occur at 272, 274. FIG. 16B, however, illustrates that the filtered signal is not only much flatter, returning to the quiescent point at about 256 ADC counts, but also, there are no false detections.

Figure 17A:
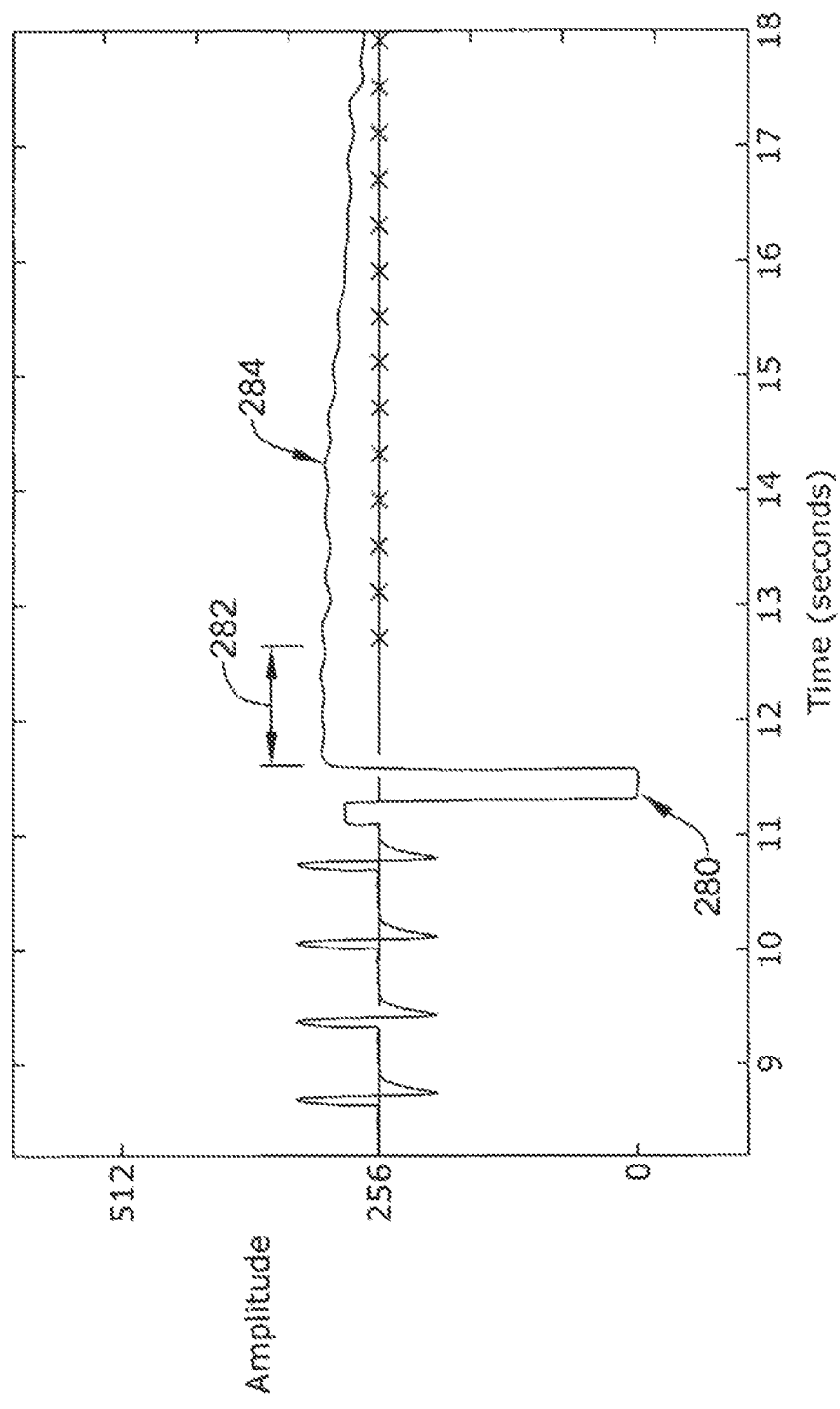
Figure 17B:
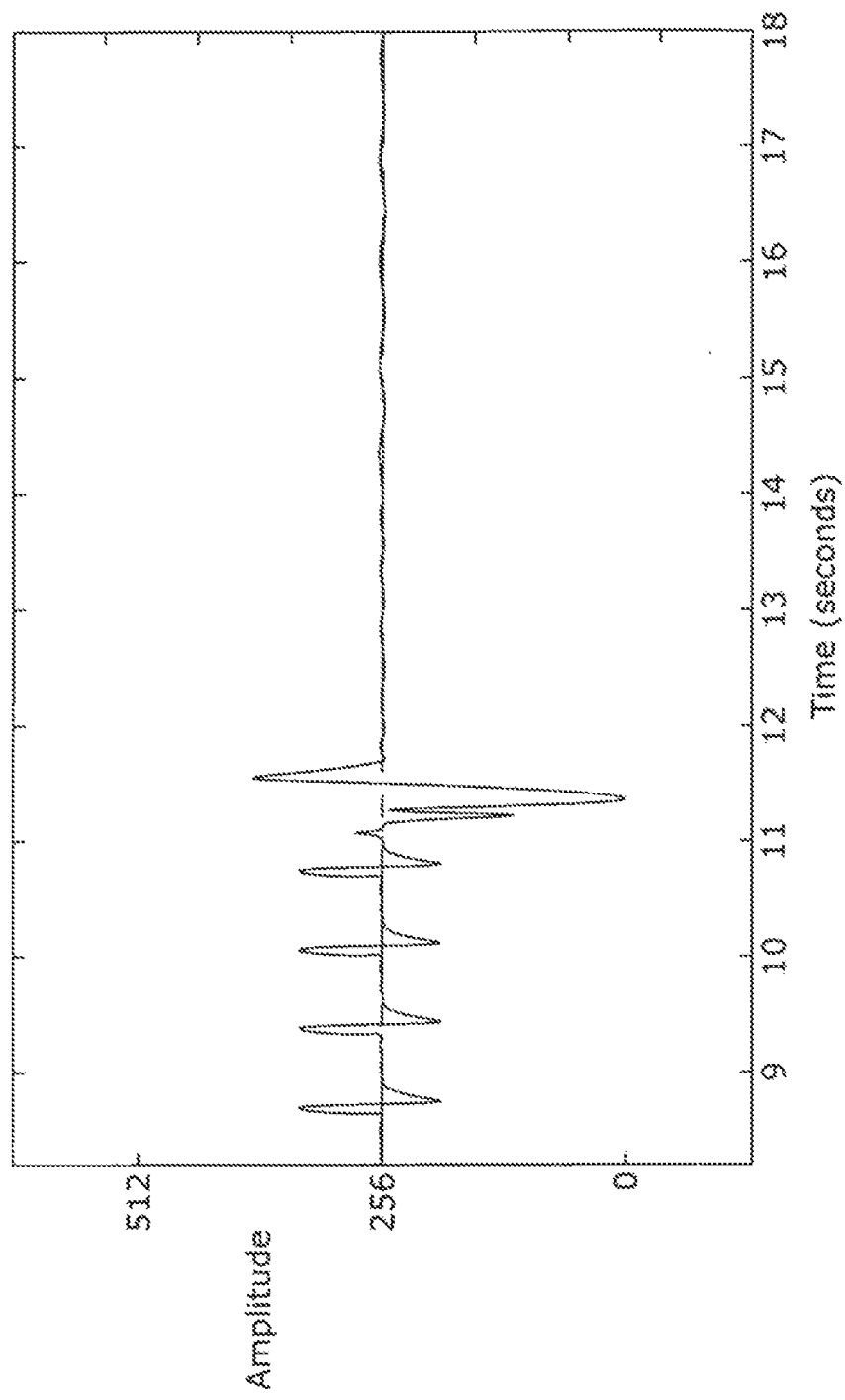

A similar approach was taken with FIGS. 17A-17B. The shock is applied at 280. A blanking period 282 occurs after the shock 280. In this instance, the after-shock signal remains relatively high for a long period of time, finally settling as t=17 and returning toward the quiescent point. The result is a large number of false detections indicated by the X's generally at 284. In contrast, FIG. 17B illustrates that the after-shock potential quickly returns to the quiescent value and remains there, averting the false detections.

Figure 18B:
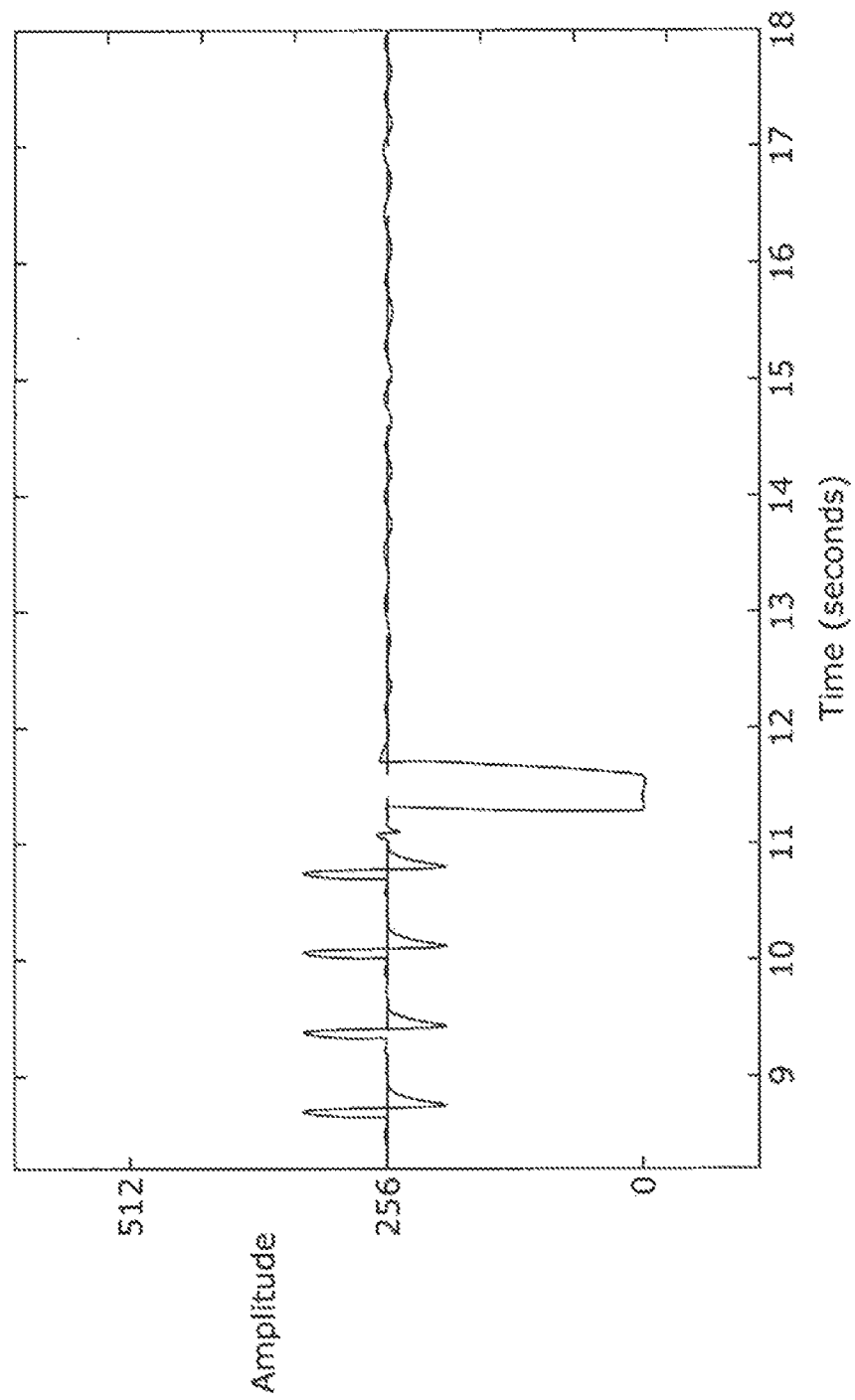

FIGS. 18A-18B again illustrate a recovery in which, without the heuristic filter in FIG. 18A, false detections 292 occur after a shock 290. These false detections are eliminated by the heuristic filter as shown in FIG. 18B.

Figure 19:
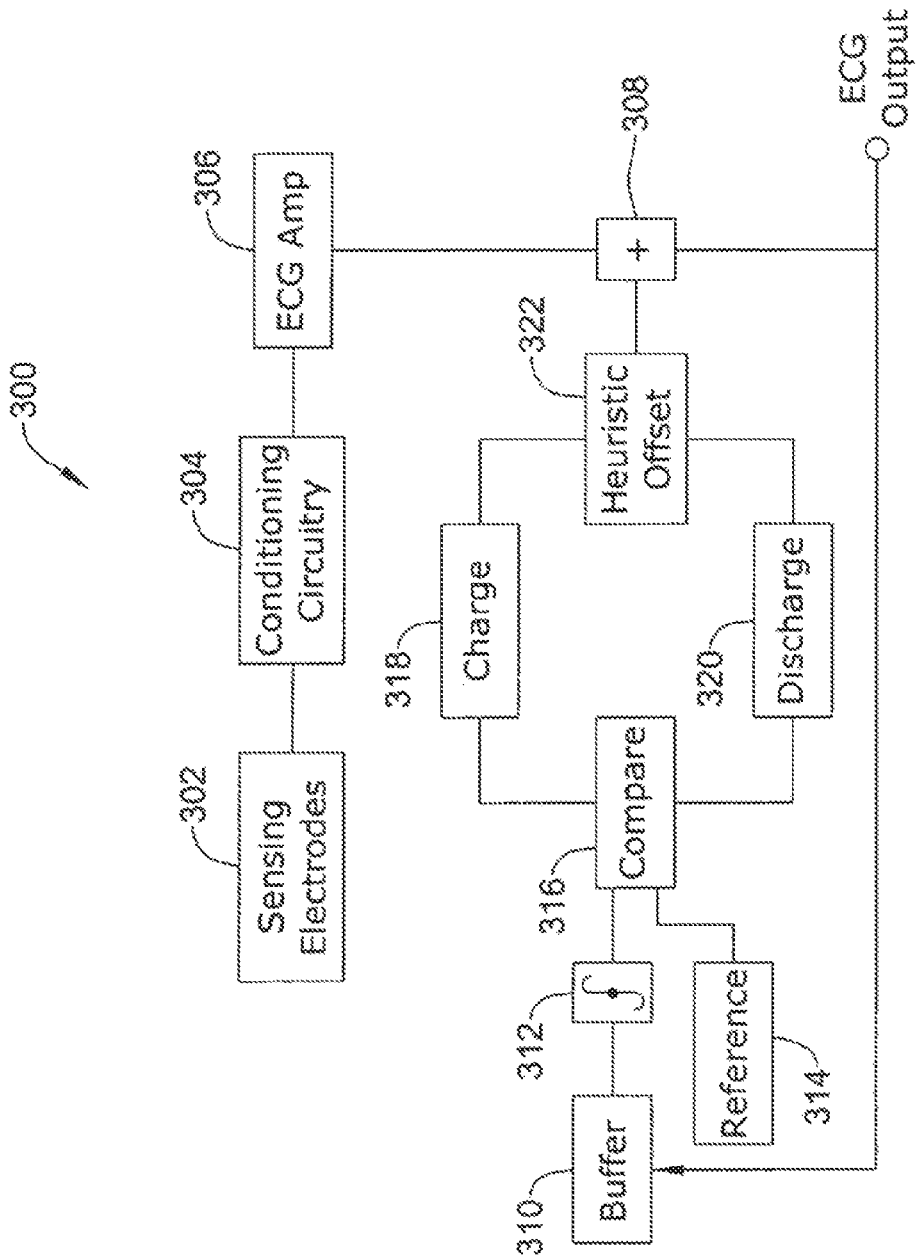
FIG. 19 illustrates an analog circuit for providing a heuristic filter.

FIG. 19 illustrates an analog circuit for providing a heuristic filter. The circuit 300 receives signal sensing electrodes 302 with conditioning circuitry 304 which in turn provides a signal to the ECG amplifier 306. The ECG amplifier 306 feeds a summer 308, which ultimately provides the ECG output. A feedback signal is taken by a buffer 310 that feeds a decaying integrator 312 (in the simplest case, the integrator 312 may be a simple RC circuit). The output of integrator 312 is compared to a stored value 314 using a comparator 316. The comparator 316 either charges 318 or discharges 320 a heuristic offset 322 depending on whether the integrator 312 provides an output that is greater than or less than the stored value 314. The heuristic offset 322 is then fed into the summer 308.

The circuit operates by observing the average value of the ECG output, as indicated by the integrator 312. Depending on the characteristics of the integrator 312 and/or buffer 310, the stored value 314 is selected to correspond to a desired quiescent point for the ECG output. The comparator 316 either increases or decreases the heuristic offset 322 in response to this comparison, thus adjusting the average ECG output. Additional circuitry may be included to increase accuracy and/or stability. If desired, rather than charging or discharging, the comparator 316 may feed an accumulator that provides a digital input to a digital-to-analog converter (DAC) that provides the heuristic offset 322 to the summer 308. In short, a feedback signal is used to center the average ECG output.

FIG. 20 illustrates the selection of a quiescent point that is off-center relative to the dynamic range of an ADC. For example, some patients demonstrate a cardiac signal that has a greater excursion in one direction than the other. This is shown in FIG. 20 where a positive excursion is substantially higher in amplitude than the negative excursion of the signal. To maximize the use of the dynamic range, this signal is placed such that the Q-point is below the center point of the ADC dynamic range. In the illustrative example, the quiescent point is selected at 210 ADC units for a 9-bit scale having a maximum range from 0-512 units.

The methods set forth above may be implemented by the use of any appropriate hardware including logic devices, controllers, processors and other suitable analog and/or digital devices or circuits. The present invention may be embodied in a software product stored on readable media including magnetic, electric and optically readable media.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of cardiac signal analysis in an implantable cardiac device system, the implantable device system comprising a plurality of electrodes adapted for implantation in a patient, the method comprising:
   sensing a signal using the electrodes; and
   applying a dynamic heuristic filter on the sensed signal to maintain a signal baseline;
   wherein the dynamic heuristic filter is configured to operate by:
   at a predefined interval, calculating an average distance to a desired quiescent point for the sensed signal, and adjusting a sensing characteristic to reduce the average distance;
   in addition, analyzing the average distance and performing one of the following:
      if the average distance is greater than a first threshold, reducing the predetermined interval if the predetermined interval is not at a preset minimum;
      if the average distance is less than a second threshold, increasing the predetermined interval if the predetermined interval is not a preset maximum; or
      else not adjusting the predetermined interval.

2. The method of claim 1, wherein the dynamic heuristic filter also operates by determining whether an event likely to cause a baseline disturbance has occurred and, if so, setting the predetermined interval to the preset minimum.

3. The method of claim 1 wherein the step of analyzing the average distance is performed at a predetermined period.

4. The method of claim 1 wherein the preset minimum is 1/1024 seconds.

5. The method of claim 1 wherein the preset maximum is 1/8 seconds.

6. The method of claim 1 wherein the step of adjusting a sensing characteristic is performed in the digital domain.

7. The method of claim 1 wherein the step of adjusting a sensing characteristic is performed by modifying an operational step of an analog to digital converter.

8. The method of claim 1 wherein the step of adjusting a sensing characteristic is performed in the analog domain.

9. An implantable cardiac rhythm management device comprising:
   at least a pair of sensing electrodes;
   operational circuitry coupled to the sensing electrodes, the operational circuitry being configured to perform a method of cardiac signal analysis comprising:
   sensing a signal using the electrodes; and
   applying a dynamic heuristic filter on the sensed signal to maintain a signal baseline;
   wherein the dynamic heuristic filter is configured to operate by:
   at a predefined interval, calculating an average distance to a desired quiescent point for the sensed signal, and adjusting a sensing characteristic to reduce the average distance;
   in addition analyzing the average distance and performing one of the following:
      if the average distance is greater than a first threshold, reducing the predetermined interval if the predetermined interval is not at a preset minimum;
      if the average distance is less than a second threshold, increasing the predetermined interval if the predetermined interval is not a preset maximum; or
      else not adjusting the predetermined interval.

10. The device of claim 9, wherein the operational circuitry is configured such that the dynamic heuristic filter also operates by determining whether an event likely to cause a baseline disturbance has occurred and, if so, setting the predetermined interval to the preset minimum.

11. The device of claim 9, wherein the operational circuitry is configured such that the step of analyzing the average distance is performed at a predetermined period.

12. The device of claim 9, wherein the operational circuitry is configured such that the preset minimum is 1/1024 seconds.

13. The device of claim 9, wherein the operational circuitry is configured such that the preset maximum is 1/8 seconds.

14. The device of claim 9, wherein the operational circuitry is configured such that the step of adjusting a sensing characteristic is performed in the digital domain.

15. The device of claim 9, wherein the operational circuitry comprises an analog to digital converter, and the operational circuitry is further configured such that the step of adjusting a sensing characteristic is performed by modifying an operational step of the analog to digital converter.

16. The device of claim 9, wherein the operational circuitry is configured such that the step of adjusting a sensing characteristic is performed in the analog domain.

17. The device of claim 9, wherein the operational circuitry comprises a microcontroller.

18. An implantable cardiac rhythm management device comprising:
   at least a pair of sensing electrodes;
   means for processing signals received from the sensing electrodes configured to perform a method of cardiac signal analysis comprising:
   sensing a signal using the electrodes; and
   applying a dynamic heuristic filter on the sensed signal to maintain a signal baseline;
   wherein the dynamic heuristic filter is configured to operate by:
   at a predefined interval, calculating an average distance to a desired quiescent point for the sensed signal, and adjusting a sensing characteristic to reduce the average distance;

in addition, analyzing the average distance and performing one of the following:
- if the average distance is greater than a first threshold, reducing the predetermined interval if the predetermined interval is not at a preset minimum;
- if the average distance is less than a second threshold, increasing the predetermined interval if the predetermined interval is not at a preset maximum; or
- else not adjusting the predetermined interval.

19. The device of claim 18, wherein the means for processing signals is configured such that the dynamic heuristic filter also operates by determining whether an event likely to cause a baseline disturbance has occurred and, if so, setting the predetermined interval to the preset minimum.

* * * * *